(12) United States Patent
Weiner et al.

(10) Patent No.: US 8,323,963 B2
(45) Date of Patent: *Dec. 4, 2012

(54) CONSTRUCTION AND USE OF GENES ENCODING PATHOGENIC EPITOPES FOR TREATMENT OF AUTOIMMUNE DISEASE

(75) Inventors: Leslie P. Weiner, Los Angeles, CA (US); Minnie McMillan, Bradbury, CA (US)

(73) Assignee: University of Southern California, Los Angeles, CA (US)

( * ) Notice: Subject to any disclaimer, the term of this patent is extended or adjusted under 35 U.S.C. 154(b) by 1266 days.

This patent is subject to a terminal disclaimer.

(21) Appl. No.: 11/488,524

(22) Filed: Jul. 17, 2006

(65) Prior Publication Data
US 2007/0104698 A1  May 10, 2007

Related U.S. Application Data

(63) Continuation-in-part of application No. 10/359,397, filed on Feb. 5, 2003, now abandoned, which is a continuation of application No. 10/098,035, filed on Mar. 14, 2002, now abandoned, which is a continuation of application No. 09/715,535, filed on Nov. 17, 2000, now abandoned, which is a continuation of application No. 08/654,737, filed on May 29, 1996, now Pat. No. 6,274,136.

(60) Provisional application No. 60/776,536, filed on Feb. 23, 2006.

(51) Int. Cl.
*C12N 5/10* (2006.01)
*A61K 48/00* (2006.01)
(52) U.S. Cl. .................. 435/325; 435/357; 424/93.21
(58) Field of Classification Search .............. 435/325, 435/357; 424/93.21
See application file for complete search history.

(56) References Cited

U.S. PATENT DOCUMENTS

| | | | |
|---|---|---|---|
| 5,264,618 A | 11/1993 | Felgner et al. | |
| 5,399,346 A | 3/1995 | Anderson et al. | |
| 5,459,127 A | 10/1995 | Felgner et al. | |
| 5,580,859 A | 12/1996 | Felgner et al. | |
| 5,589,466 A | 12/1996 | Felgner et al. | |
| 5,716,826 A | 2/1998 | Gruber et al. | |
| 5,756,300 A * | 5/1998 | Seitz et al. | 435/7.1 |
| 6,036,957 A * | 3/2000 | Weiner et al. | 424/184.1 |
| 6,060,309 A * | 5/2000 | Kindsvogel et al. | 435/325 |
| 6,274,136 B1 * | 8/2001 | Weiner et al. | 424/93.21 |
| 7,030,098 B2 * | 4/2006 | Steinman et al. | 514/44 R |

OTHER PUBLICATIONS

Vatakis, D. N. (2003) Dissertation Abstracts International, vol. 65/01-B, 150 pages (Parts 1-3).*
Weiner et al. (2004) Ann. Neurol., vol. 55, 390-399.*
Louie et al. (2005) Gene Therapy, vol. 12, 1145-1153.*
Barbarese et al. (1988) J. Neurochem., vol. 51, 1737-1745.*
Genbank accession No. AAB24648 (1993) "human leukocyte antigen beta chain DR molecule, HLA-DRB1 (DRB1 allele 1501) [human, peptide partial, 24 aa]".*
Sequence alignment between SEQ ID No. 10 and sequence disclosed in 6,036,957.*
Al-Sabbagh, A. et al., "Antigen-driven tissue-specific suppression following oral tolerance: orally administered myelin basic protein suppresses proteolipid protein-induced experimental autoimmune encephalomyelitis in the SJL mouse," Eur. J. Immunology, Sep. 1994, 24(9):2104-2109.
Barnett, L. et al. "Virus encoding an encephalitogenic peptide protects mice from experimental allergic encephalomyelitis", Journal of Neuroimmunology, Feb. 1996, 64:163-173.
Crystal, R. G. "Transfer of genes to humans: Early lessons and obstacles to success", Science, Oct. 1995, 270:404-410.
Donnelly, J.J. et al., "Immunization with DNA," Journal of Immunological Methods, Aug. 29, 1994, 176:145-152.
Fynan, E.F. et al., "DNA Vaccines: Protective immunizations by parenteral, mucosal, and gene-gun inoculations," Proc. Natl. Acad. Sci. U.S.A., Dec. 1993, 90:11478-11482.
Gaur, A. et al., "Amelioration of autoimmune encephalomyelitis by myelin basic protein synthetic peptide-induced anergy," Science, Nov. 27, 1992, 258(5087):1491-1494.
Javed, N. H. et al., "Exquisite peptide specificity of oral tolerance in experimental autoimmune encephalomyelitis", Journal of Immunology, Aug. 1, 1995, 155(3):1599-1605.
Kalden, J.R. et al. "Immunological Treatment of Autoimmune Diseases", Advances in Immunology, 1998, 68:333-418.
Lemay, G. et al. "Fusion of a cleavable signal peptide to the ectodomain of neutral endopeptidase (EC 3.4.24.11) results in the secretion of an active enzyme in COS-1 cells", Journal of Biological Chemistry, Sep. 1989, 264 (26):15620-15623.
Miller, S.D. et al. "The immunopathogenesis and regulation of T-cell-mediated demyelinating diseases", Immunology Today, Aug. 1994, 15(8):356-360. Sep. 18, 2009.
Willenborg, D.O. et al., "Approaches to the treatment of central nervous system autoimmune disease using specific neuroantigen", Immunology and Cell Biology, Feb. 1998, 76(1):91-103. Wraith, D.C., "Induction of antigen-specific unresponsiveness with synthetic peptides: specific immunotherapy for treatment of allergic and autoimmune conditions," International Archives of Allergy and Immunology, Dec. 1995, 108(4):355-359.
Yu, M. et al., "A predictable sequential determinant spreading cascade invariably accompanies progression of experimental autoimmune encephalomyelitis: a basis for peptide-specific therapy after onset of clinical disease," J. of Experimental Medicine, Apr. 1, 1996, 183(4):1777-1788.

* cited by examiner

*Primary Examiner* — Anne Marie S Wehbe
(74) *Attorney, Agent, or Firm* — Bingham McCutchen LLP

(57) ABSTRACT

This invention relates to the design and construction of a gene encoding an encephalogenic epitope of proteolipid protein (PLP), design and construction of a gene encoding an encephalogenic epitope of myelin based protein (MBP), to methods of expression of a PLP epitope, to methods of expression of a MBP epitope, to methods of in vivo secretion of a PLP epitope, and to methods of transferring the partial PLP gene to a host to ameliorate the progression of an immune response to self antigens derived from myelin proteins, to methods of in vivo secretion of a MBP epitope, and to methods of transferring the partial MBP gene to a host to ameliorate the progression of an immune response to self antigens derived from myelin proteins.

20 Claims, 23 Drawing Sheets

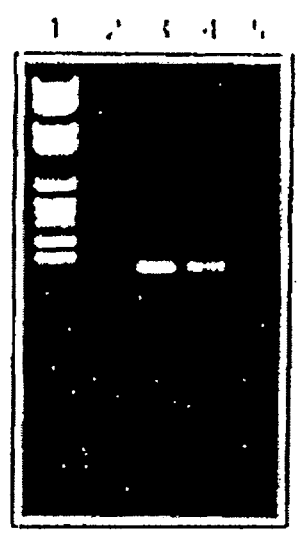
Figure 4. mRNA expression levels as detected by reverse transcriptase PCR.

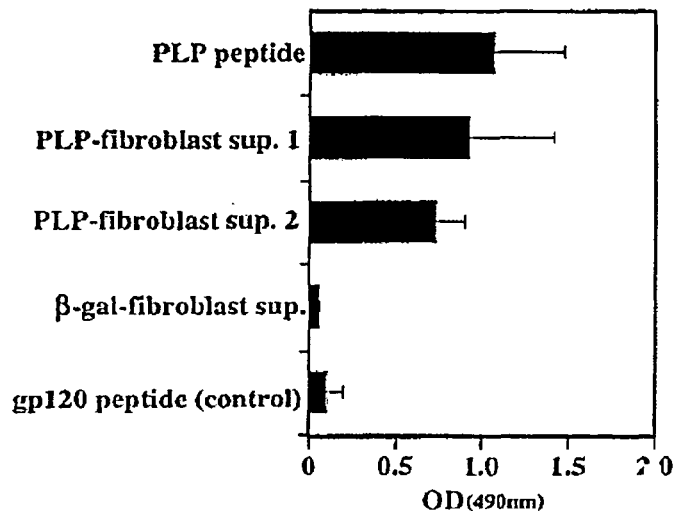

| Sample | OD of reaction product measured at 490 nm |
|---|---|
| 1. PLP peptide 139-151 | 1.06±0.41 |
| 2. HIV gp120 peptide control | 0.10±0.09 |
| 3. Supernatant of SJL fibroblasts transduced with PLP retrovirus. Sample I | 0.92±0.50 |
| 4. Supernatant of SJL cultured fibroblasts transduced with PLP retrovirus. Sample II | 0.73±0.17 |
| 5. Supernatant of cultured fibroblasts transduced with β-galactosidase (LacZ) construct | 0.05±0.01 |

1. PLP and HIV gp120 peptides used at a concentration of 5 ug/ml.
2. All supernatants used undiluted.
3. Primary monoclonal antibody was used as an undiluted hybridoma supernatant.
4. Peroxidase conjugated secondary goat anti-antibody used at a dilution 1:500.

Figure 5. ELISA assays on transduced fibroblast supernatants

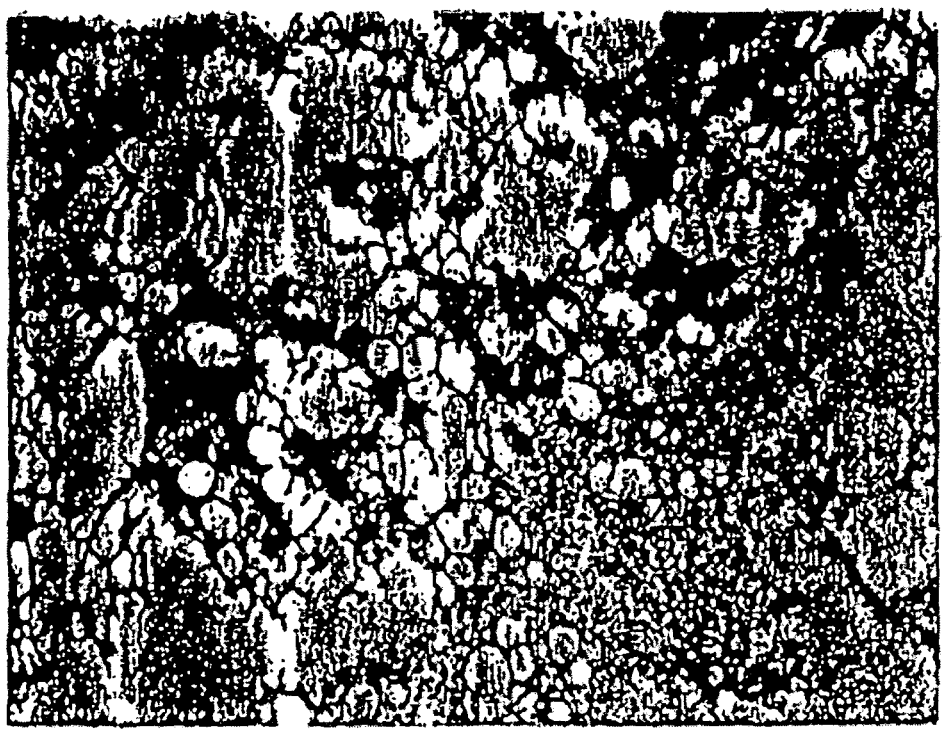
Figure 6. B-Gal expression in transduced fibroblasts

FIGURE 7

| | |
|---|---|
| Grade 0 | no abnormality |
| Grade 1 | slow, sluggish |
| Grade 2 | limp tail |
| Grade 3 | limp tail, hand/limb weakness, waddling gait |
| Grade 4 | partial hind limb paralysis |
| Grade 5 | complete hind limb paralysis |
| Grade 6 | animal immobile |
| Grade 7 | moribund |

Figure 7. Clinical Scores Chronic EAE

FIGURE 8

Histological Scoring System

1+   mild (1-3 small foci)

2+   moderate (more than 3-7 foci containing at least 10)

3+   severe (large foci of 15 to 25 cells with perivascular and meningeal collections)

4+   severe with necrosis and demyelination

Figure 12. Proliferation assays using A) four control EAE mice and B) four EAE mice treated with PLP-expressing fibroblasts Figure 13. Proliferation assays in the absence (left-hand histogram) and presence (right-hand histogram) of IL-2 using A) four EAE control mice and B) four EAE mice treated with PLP-expressing fibroblasts Figure 1 Schematic diagram of construct encoding MBP amino acids 71–111. The sources of the sequences are indicated in boxes beneath the text.

CONSTRUCTION AND USE OF GENES ENCODING PATHOGENIC EPITOPES FOR TREATMENT OF AUTOIMMUNE DISEASE

CROSS-REFERENCE TO RELATED APPLICATIONS

This application is continuation-in-part claiming priority to U.S. Provisional Application No. 60/776,536 filed Feb. 23, 2006 and U.S. application Ser. No. 10/359,397 filed Feb. 5, 2003, now abandoned which is a continuation of U.S. application Ser. No. 10/098,035 filed Mar. 14, 2002, now abandoned, which is a continuation of U.S. application Ser. No. 09/715,535 filed Nov. 17, 2000, now abandoned, which in turn is a continuation of U.S. application Ser. No. 08/654,737 filed May 29, 1996, now U.S. Pat. No. 6,274,136. The contents of all of these priority applications are hereby incorporated by reference into the present disclosure.

FIELD OF THE INVENTION

This invention relates generally to the field of immunotherapy and to the preparation and use of engineered cells having the ability to restore tolerance to self antigens in patients suffering from autoimmune disease.

BACKGROUND OF THE INVENTION

The immune system can respond in two ways when exposed to an antigen. A positive response leads to differentiation and proliferation of T and B cells, antibody production, killer T cells and to immunologic memory. A negative response leads to suppression, inactivation, or silencing of specific lymphocytes and to tolerance. Tolerance can be defined as the failure of a host to mount an immune response against a specific antigen. Normally, an organism is tolerant of its own antigens.

Autoimmune diseases are thought to result from an uncontrolled immune response directed against self antigens. In patients with multiple sclerosis (MS), for example, there is evidence that this attack is against the white matter of the central nervous system and more particularly to white matter proteins. Ultimately, the myelin sheath surrounding the axons is destroyed. This can result in paralysis, sensory deficits and visual problems. MS is also characterized by a lymphocyte and mononuclear cell infiltrate in the brain.

Susceptibility genes for MS have not been clearly identified, although the major histocompatibility complex HLA, particularly the DR2 haplotype, has been implicated. [Barcellos L. F., et al., Brain, 125: 150-158 (2002); Barcellos L. F., et al., Am. J. Hum. Genet., 72: 710-716 (2003); Coraddu, F., et al., Neurogenetics, 2: 24-33 (1998); Jersild, C., Svejgaard, A., Fog, T., Lancet, 1: 1240-1241 (1972).]

Autoreactive myelin-specific T cells, however, have been isolated from MS patients, although T cells of the same specificity have been detected in normal individuals. [LaSalle, J. M., et al., J. Immunol., 147:774-780 (1991); LaSalle, J. M., et al., J. Exp. Med., 176:177-186 (1992), Correale, J., et al., Neurology, 45:1370-1378 (1995).] Myelin-specific activated CD4 T cells secreting inflammatory cytokines (Th1 cells) appear to play a significant role in orchestrating myelin destruction. [Hemmer, B., Archelos, J. J., Hartung, H. P., Nat. Rev. Neurosci., 3: 291-301 (2002); Prat, E., Martin, R. J., Rehabil. Res. Dev., 39: 187-199 (2002).]

Some of the therapies described herein are aimed at specifically silencing these myelin-specific activated CD4 T cells, so they no longer respond to myelin antigen. [Baker, D., Hankey, D. J., Gene Ther. 10: 844-853 (2003); Furlan, R., Pluchino, S., Martino, G., Curr. Opin. Neurol., 16: 385-392 (2003); Mathisen, P. M., Tuohy, V. K., J. Clin. Immunol., 20: 327-333 (2000); Seroogy, C. M., Fathman, C. G., Gene Ther., 7: 9-13 (2000); Tarner, I. H., et al., Ann. N. Y. Acad. Sci. 998: 512-519 (2003).] Presently, the myelin proteins thought to be the target of an immune response in MS include, but are not necessarily limited to, myelin basic protein (MBP), proteolipid protein (PLP), and myelin-oligodendrocyte glycoprotein (MOG). Individuals who do not mount an autoimmune response to self proteins are thought to have control over these responses and are believed to be "tolerant" of self antigens. The evidence, therefore, that MS is caused by pathogenic T cells is necessarily indirect, but the close resemblance of the characteristics of this disease compared to those of the murine model, experimental autoimmune encephalomyelitis (EAE), suggest that MS is indeed caused by an aberrant immune response mediated by T cells.

The murine experimental autoimmune encephalomyelitis (EAE) mouse model for MS displays many of the same histopathological and clinical characteristics as the relapsing remitting forms of MS. [Zamvil, S. S., et al., Ann Rev. Immunol., 8:579-621 (1990); Brown, A. M., McFarlin, D. E., Lab. Invest. 45: 278-284 (1981); Kuchroo, V. K., et al., Annu. Rev. Immunol. 20: 101-123 (2002); Zhang. J., et al., J. Exp. Med., 179: 973-984 (1994).] EAE can be induced in SJL mice by injection of mouse spinal cord homogenate (MSCH), MBP, PLP, synthetic peptides whose sequences correspond to the major encephalogenic epitopes of myelin basic protein, MBP 84-104, proteolipid protein, PLP 139-151, or by adoptive transfer of activated CD4$^+$ T$_{H1}$, but not T$_{H2}$ cells specific for encephalogenic epitopes. For example, EAE was induced in female SJL/J mice that was mediated by CD4$^+$ T cells specific for proteolipid protein (PLP) amino acids 139-151. [Sobel, R. A., Greer, J. M., Kuchroo, V. K., Neurochem. Res., 19: 915-921(1994); Tuohy, V. K., et al., J. Immunol., 142: 1523-1527 (1989); Tuohy, V. K., et al., J. Neuroimmunol., 39: 67-74 (1992).] In subsequent relapses, T cells specific for other encephalogenic epitopes, such as myelin basic protein (MBP) amino acids 84-104, have also been demonstrated. [McRae, B. L., Vanderlugt, C. L., Dal Canto, M. C., Miller, S. D., J. Exp. Med., 182: 75-85 (1995); Vanderlugt, C. L., et al., J. Immunol. 164: 670-678 (2000).]

The course of EAE in mice closely resembles clinical manifestations and pathology of relapsing and remitting MS in humans. This model is well known in the art, it is used to explore autoimmune mechanisms, test immunomodulating drugs directed at MS, and is the accepted analog to human multiple sclerosis. The major encephalogenic epitopes of myelin-derived sequences in EAE, such as MBP, can also activate human T cells of several different haplotypes including HLA-DR2. [Martin, R., et al., J. Exp. Med., 173:19-24 (1992).] The experimental disease is characterized by a relapsing-remitting course (R-EAE) of neurological dysfunction, perivascular mononuclear infiltration and demyelination. The mechanism of CNS damage appears to be mediated by inflammatory cytokines which can activate additional monocytes and macrophages non-specifically. [Blalock, J. E., The Immunologist, 2:8-15 (1994).]

Although the initial attack in EAE can be induced by the administration of either T cells specific for MBP or for PLP, close examination of reactivities of T cells in the primary and subsequent relapses demonstrated the presence of T cells which interact with specificities other than the inducing epitopes. This expansion of encephalogenic epitopes is termed "determinant spreading" or "epitope spreading."

[Miller, S. D. and Karpus, W. J., Immunology Today, 15:356-361 (1994); Lehman, P. V., et al., Nature, 358:155-157 (1992); Jiang, H., et al., Science, 256:1213-1215 (1992); Tuohy, V. K., et al., Immunol. Rev., 164: 93-100 (1998); Vanderlugt, C. L. and Miller, S. D., Nat. Rev. Immunol. 2: 85-95 (2002).] Antigen specific treatment would therefore, be expected to be more effective when administered early in the course of the disease, before the onset of increasing epitope complexity and eventual non-specific inflammation.

A way to treat autoimmune disease is the use of immunotherapy that can restore tolerance without suppressing the entire immune system which can lead to complications such as infection, hemorrhage, and cancer. Drugs currently used to treat autoimmune diseases have only been partially effective. Many of these drugs are non-specific immunosuppressive agents, anti-inflammatory agents or drugs which can block cell proliferation or depress proinflammatory cytokines or immunocytotoxic drugs. [Goodin, D. S., et al., Neurology, 58: 169-178 (2002); Hohlfeld, R. and Wiendl, H., Ann. Neurol., 49: 281-284 (2001); Martin, R., et al., Nat. Immunol., 2: 785-788 (2001); Steinman, L., Curr. Opin. Immunol., 13: 597-600 (2001).] Currently, immunomodulatory agents, such as interferon $\beta$-1A and 1B and glatiramer acetate are used to treat MS. In general, these agents are only effective for a limited duration and are subject to significant complications.

Thus it is desirable to suppress the immune system in a more specific way to control the response to self-antigens and theoretically "cure" the disease without down-regulating the entire immune system. In particular, a therapeutic approach that can downregulate pathogenic T cells while leaving the immune response otherwise intact may be an ideal solution. [von Herrath, M. G. and Harrison, L. C., Nat. Rev. Immunol., 3: 223-232 (2003).] Several specific immunotherapies have been hypothesized and tested in recent years, many of which are impractical or do not work in humans. For example, high affinity peptides can be synthesized which interact with MHC class II molecules and prevent the binding of encephalogenic peptides, thereby preventing the activation of pathogenic T cells. [Franco, A. et al., The Immunologist, 2:97-102 (1994).] This approach is disadvantageous in that it is difficult to obtain effective concentrations of inhibitor peptides in vivo. [Ishioka, G. Y., et al., J. Immunol., 152:4310-4319 (1994).] In an alternate strategy, peptides that are analogs of encephalogenic sequences have been shown to antagonize the T cell receptors of antigen-specific T cells, rendering them unreactive, although the exact mechanism is at present unknown. [Jameson, S. C., el al., J. Exp. Med., 177:1541-1550 (1993); Karin, N., et al., J. Exp. Med., 180:2227-2237 (1994); Kuchroo, V. K., et al., J. Immunol., 153:3326-3336 (1994).] Oral administration of myelin has been tested and found to induce a state of immunological unresponsiveness thought to be mediated by the induction of suppressor T cell or of anergy. [Weiner, H. L., et al., Annu. Rev. Immunol., 12:809-837 (1994); Whitacre, C. C., et al., J. Immunol., 147:2155-2163 (1991); Khoury, S. J., et al., J. Exp. Med., 176:1355-1364 (1992).]

In recent years, a variety of gene therapy strategies have also been used in EAE in mice. [Baker, D., Hankey, D. J., Gene Ther. 10: 844-853 (2003); Furlan, R., et al., Curr. Opin. Neurol. 16: 385-392 (2003); Mathisen, P. M. and Tuohy, V. K., J. Clin. Immunol., 20: 327-333 (2000); Seroogy, C. M. and Fathman, C. G., Gene Ther., 7: 9-13 (2000); Tamer, I. H., et al. Ann. N. Y. Acad. Sci. 998: 512-519 (2003).] These strategies were designed to prevent EAE rather than cure it. One gene therapy strategy used plasmids encoding the IL-4 gene together with myelin antigen, the PLP (139-151) epitope or myelin oligodendrocyte glycoprotein (MOG), which have been shown to elicit either protection in the case of PLP or amelioration of established disease in the case of MOG. [Garren. H., et al., Immunity, 15: 15-22 (2001).] Another approach has been to genetically modify antigen-specific T cells to deliver immunoregulatory molecules. [Chen, L. Z., et al., Proc Natl Acad Sci USA, 95: 12516-12521 (1998); Costa, G. L., et al., J. Immunol., 167: 2379-2387 (2001); Mathisen, P. M., et al., J. Exp. Med. 186: 159-164 (1997); Shaw, M. K., et al., J. Exp. Med., 185: 1711-1714 (1997); Yin, L., et al., J. Immunol., 167: 6105-6112 (2001).] In yet another approach, B cells were transduced with a vector encoding PLP (100-154) as well as B cells expressing a MBP-Ig fusion protein were shown to ameliorate ongoing disease. [Chen, C. C., et al., Blood, 103: 4616-4618 (2004); Melo, M. E., et al., J. Immunol., 168: 4788-4795 (2002).] Yet, another strategy includes the direct injection of naked DNA encoding anti-inflammatory cytokines. [Baker, D. and Hankey, D. J., Gene Ther., 10: 844-853 (2003).]

None of these strategies, however, have been able to effect a "cure." As stated earlier, the standard of care currently has patients treated early in the course of disease usually with immunomodulatory molecules. The two commonly used immunomodulatory molecules include a synthetic amino acid polymer COPAXONE® (Teva Neuroscience) and the cytokine, interferon-$\beta$, which is manufactured with varying degrees of glycosylation and is marketed under the names of BETASERON® (Berlex/Schering), AVONEX® (Biogen) and REBIF® (Serono). At best these drugs are 30% effective and their side effects can be very significant and result in cessation of treatment. Interferon-$\beta$ can cause flu-like symptoms, depression and liver damage. Patients can also generate antibodies which neutralize the cytokine thereby negating its therapeutic effect. COPAXONE® can cause allergic reactions which again results in termination of treatment.

In February 2005, a monoclonal antibody to the integrin VLA-4, called TYSABRI®, (Biogen and Elan) was withdrawn from market because two patients receiving AVONEX® together with TYSABRI® died from progressive multifocal leukoencephalopathy, a rare demyelinating disease caused by JC virus. The FDA is considering returning this drug to market because it proved to be 65% effective. It seems unlikely, however, that this molecule will be widely prescribed due to the extreme side effects.

Further, the cost of interferon-beta is $10-14,000 per patient per year while the price of COPAXONE® is $12-13,000 per patient per year. Thus, improvements are needed to treat MS and other autoimmune disorders with an effective, immunospecific approach.

SUMMARY OF THE INVENTION

The present invention addresses the disadvantages present in the prior art. In general, the invention is based on the discovery that recombinant DNA technology and cell transfer may be employed to restore tolerance to one's own tissues by silencing T cells. The present invention provides a method comprising introducing a cell comprising a polynucleotide encoding an antigenic amino acid sequence into a patient, the cell expressing in the patient a therapeutically effective amount of the antigenic amino acid sequence to silence pathogenic T cells to the expressed antigenic amino acid sequence. In another embodiment, the patient is a mammal. In a further embodiment, the patient is a human. In yet another embodiment, the cell is allogeneic to the patient. In an additional embodiment, the cell that is allogeneic to the patient is sequestered in a chamber. In a further embodiment, the chamber is implanted into the patient subcutaneously. In an embodiment, the cell is a fibroblast. In a further embodiment, the fibroblast is allogeneic to the patient. In yet a further embodiment, the allogeneic fibroblast is sequestered in a chamber. In a further embodiment, the allogeneic fibroblast that is sequestered in a chamber is implanted into the patient subcutaneously. In another embodiment, the antigenic amino acid sequence is a portion of a complex antigenic molecule. In yet another embodiment, the antigenic amino acid sequence is encoded by nucleic acid sequence of SEQ ID NO: 10. In another embodiment, the antigenic amino acid sequence comprises an encephalogenic amino acid epitope. In a further embodiment, the antigenic amino acid sequence is encoded by nucleic acid sequence of SEQ ID NO: 11. In yet a further embodiment, the encephalogenic amino acid epitope is selected from the group consisting of myelin basic protein, myelin-oligodendrocyte glycoprotein, and proteolipid protein. In another embodiment the patient has multiple sclerosis. In yet another embodiment, the antigenic amino acid sequence further comprises a leader sequence. In yet another embodiment, the leader sequence is derived from a secreted protein. In a further embodiment, the secreted protein is a chemokine. In a particular embodiment, the leader sequence is encoded by nucleic acid sequence of SEQ ID NO: 14. In an additional embodiment, the patient has a disease that is selected from the group consisting of multiple sclerosis, rheumatoid arthritis, systemic lupus erythematosus, psoriasis, juvenile onset diabetes, thyroid disease, myasthenia gravis, and chronic inflammatory demyelinating polyneuropathy. In a particular embodiment, patient has the disease is multiple sclerosis. In a further embodiment, a recombinant vector is used to transduce the antigenic amino acid sequence into the cell. In another embodiment, the vector is a viral vector. In yet another embodiment, the antigenic amino acid sequence has a carboxyl terminus and further comprises at least one amino acid located at the carboxyl terminus with a positive charge. In a particular embodiment, the amino acid located at the carboxyl terminus of the antigenic amino acid sequence is a lysine.

The present invention also provides a composition comprising a cell transduced with a polynucleotide encoding an antigenic amino acid sequence, wherein the cell expresses a therapeutically effective amount of the antigenic amino acid sequence able to silence pathogenic T-cells to the expressed antigenic amino acid sequence in a patient. In a particular embodiment the patient is a mammal. In a further embodiment the patient is a human. In yet another embodiment, the cell is allogeneic to the patient. In another embodiment, the cell is sequestered in a chamber. In a further embodiment, the cell that is sequestered in a chamber is implanted in the patient subcutaneously. In another embodiment, the cell is a fibroblast. In yet another embodiment, the fibroblast is allogeneic to the patient. In a further embodiment, the fibroblast is sequestered in a chamber. In yet a further embodiment, the fibroblast that is sequestered in a chamber is implanted into the patient subcutaneously. In another embodiment, the antigenic amino acid is a portion of a complex antigenic molecule. In another embodiment, the antigenic amino acid sequence is encoded by nucleic acid sequence of SEQ ID NO: 10. In yet another embodiment, the antigenic amino acid sequence comprises an encephalogenic amino acid epitope. In a further embodiment, the antigenic amino acid sequence is encoded by nucleic acid sequence of SEQ ID NO: 11. In another embodiment, the encephalogenic amino acid epitope is selected from the group consisting of myelin basic protein, myelin-oligodendrocyte glycoprotein, and proteolipid protein. In another embodiment, the patient has multiple sclerosis. In another embodiment, the antigenic amino acid sequence further comprises a leader sequence. In a further embodiment, the leader sequence is derived from a secreted protein. In yet a further embodiment, the secreted protein is a chemokine. In a particular embodiment, the leader sequence is encoded by nucleic acid sequence of SEQ ID NO: 9. In another embodiment, the patient has a disease that is selected from the group consisting of multiple sclerosis, rheumatoid arthritis, systemic lupus erythematosus, psoriasis, juvenile onset diabetes, Sjogren's disease, thyroid disease, myasthenia gravis, and chronic inflammatory demyelinating polyneuropathy. In a further embodiment, the patient has multiple sclerosis. In another embodiment, a recombinant vector is used to transduce the antigenic amino acid sequence into the cell. In yet another embodiment, the vector is a viral vector. In a further embodiment, the viral vector is a retroviral vector. In another embodiment, the antigenic amino acid sequence has a carboxyl terminus and further comprises at least one amino acid located at the carboxyl terminus with a positive charge. In a further embodiment, the amino acid located at the carboxyl terminus is a lysine.

The present invention also provides a kit comprising a cell transduced with a polynucleotide encoding an antigenic amino acid sequence, wherein the cell expresses a therapeutically effective amount of the antigenic amino acid sequence to silence pathogenic T-cells to the antigenic amino acid sequence; a container therefore; and instructions for use. In a another embodiment the kit further comprises a chamber. In another embodiment, the cell is an allogeneic cell to a patient. In a further embodiment, the cell is a fibroblast. In another embodiment, the antigenic amino acid sequence is a portion of a complex antigenic molecule. In a further embodiment, the antigenic amino acid sequence is encoded by nucleic acid sequence of SEQ ID NO: 10. In yet another embodiment, the antigenic amino acid sequence comprises an encephalogenic amino acid epitope. In a particular embodiment, the encephalogenic amino acid epitope is selected from the group consisting of myelin basic protein, myelin-oligodendrocyte glycoprotein, and proteolipid protein. In another embodiment, the encephalogenic amino acid is encoded by nucleic acid sequence of SEQ ID NO: 11. In a further embodiment, the antigenic amino acid sequence further comprises a leader sequence. In yet a further embodiment, the leader sequence is derived from a secreted protein. In a particular embodiment the secreted protein is a chemokine. In another embodiment, the antigenic amino acid sequence has a carboxyl terminus and further comprises at least one amino acid located at the carboxyl terminus with a positive charge. In yet another embodiment, the amino acid located at the carboxyl terminus of the antigenic amino acid sequence is a lysine.

BRIEF DESCRIPTION OF THE DRAWINGS

FIG. 4 shows the level of mRNA expressed in transfected and transduced SJL fibroblast cells as detected by reverse transcriptase PCR. Lane 1 is molecular weight standards, Lane 2 is Negative control from mock transfection, Lane 3 is positive control-PLP-gene plasmid, Lane 4 is cDNA from PLP-transfected SJL fibroblasts, Lane 5 is cDNA from PLP transduced SJL fibroblasts (the band is very faint, but present).

FIG. 5 demonstrates the level of PLP protein in the supernatants of transduced fibroblasts as detected by ELISA. The graph shows the data on the table. The absorbance at 490 nm is plotted on the abscissa and the identities of the supernatants of the transduced cells, or control peptides are plotted on the ordinate.

FIG. 6 demonstrates the level of B-Gal expression in transduced fibroblasts.

FIG. 7 illustrates the clinical scoring system for chronic EAE

FIG. 8 illustrates the histological scoring system for EAE.

FIG. 19a shows arrows to particular structures and FIG. 19b is a magnified portion of FIG. 19a.

DETAILED DESCRIPTION OF THE INVENTION

The present invention provides methods and compositions relating to engineered cells to restore tolerance to self antigens in patients suffering from autoimmune disease. The engineered cells can be any mammalian cell, including but not limited to, human, murine, rat, rodent, bovine, porcine, ovine, simian, canine, feline, and primate cells. Further, the engineered cells can be allogeneic to the patient.

Human gene therapy was initially conceived to treat genetic diseases by the introduction of the appropriate functional gene into cells. It now encompasses the treatment of complex acquired diseases such as cancer, cardiovascular ailments and autoimmune disorders. [Anderson, W. F., Science, 256: 808-813 (1992); Balicki, D., Beutler, E., Medicine (Baltimore), 81: 69-86 (2002); Anderson, W. F., Hum. Gene Ther., 13: 1261-1262 (2002); Miller, A. D., Nature, 357: 455-460 (1992).] Embodiments of the present invention include gene therapy strategies using cells engineered to deliver therapeutic molecules in order to treat patients suffering from the most common autoimmune disease of the central nervous system, such as, but not limited to, multiple sclerosis (MS).

Figure 21:
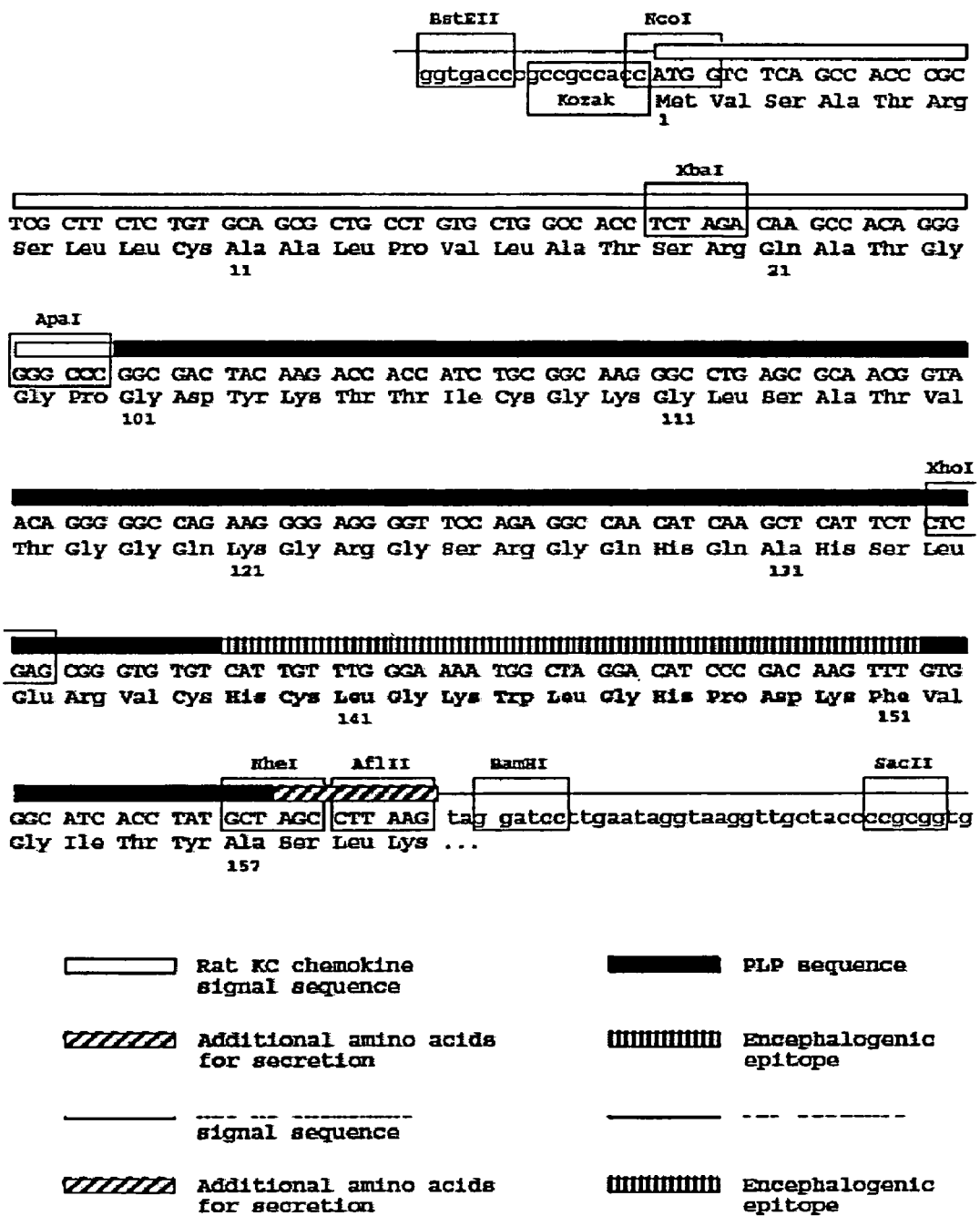
FIG. 21 is a map showing a construct having a nucleotide sequence corresponding to SEQ ID NO: 37 and encoding a polypeptide having an amino acid sequence corresponding to SEQ ID NO: 38. The construct encodes a partial PLP gene product, amino acids 101-157 (SEQ ID NO: 3), with a RAT KC chemokine leader sequence (encoded by SEQ ID NO: 9), and additional lysine for secretion (encoded by SEQ ID NO: 12). Serine and leucine are present for introduction of the restriction site.

Recombinantly-introduced genes will either be in the form of a synthetic oligonucleotide, a cDNA gene (i.e., they will not contain introns), a partial copy of a genomic gene sequence, or a hybrid gene which is a fusion of two or more gene sequences. Optionally, the gene may be linked to one or more nucleotide sequence capable of directing expression of the gene product. Sequence elements capable of effecting expression of a gene or gene product include, but are not limited to promoters, enhancer elements, transcription termination signals, polyadenylation sites, a Kozak box sequence to ensure efficient translation, and leader sequences. Optionally, the gene sequence can include restriction sites to enable the insertion of additional gene sequences, such as, but not limited to, a gene sequence encoding a positively charged carboxyl terminus. For example, a gene sequence encoding a lysine permits the protein to be secreted. Optionally, the gene may contain a leader sequence to ensure the gene product is synthesized into the endoplasmic reticulum for later constitutive secretion. Optionally, the gene may contain additional positively charged amino acid to enhance secretion of the gene product. These positively charged amino acids include, but are not limited to, lysine, arginine, histidine, either alone or in combination with each other or in combination with other amino acids. See FIGS. 1, 14 and 21.

Recombinantly-introduced genes carried by the engineered cells can encode one or more epitope, fragment, domain, or mini-protein portion of a protein antigen. Examples of suitable proteins from which an epitope, fragment, domain, or mini-protein may be derived include, but are not limited to, myelin proteins, acetylcholine receptor, TSH receptor, insulin, and collagen.

Protein self-antigens which are the target of an autoimmune response are highly conserved both among and between species. Thus, although the invention will primarily be used to treat humans it can also be used to treat animals. Examples of T cell mediated autoimmune diseases that may be treated using the invention include, but are not limited to, multiple sclerosis, myasthenia gravis, systemic lupus erythematosus, psoriasis, juvenile onset diabetes, rheumatoid arthritis, thyroid disease, Sjögren's disease, and chronic inflammatory demyelinating polyneuropathy (CIDP).

Expression vectors are generally deoxyribonucleotide molecules engineered for controlled expression of one or more desired genes. The vectors may comprise one or more nucleotide sequences operably linked to a gene to control expression of the desired gene or genes. There are an abundance of expression vectors available and one skilled in the art could easily select an appropriate vector. In addition, standard laboratory manuals on genetic engineering provide recombinant DNA methods and methods for making and using expression vectors. Optionally, the vector may encode a selectable marker, for example, antibiotic resistance.

The gene can be inserted into the mammalian cell using any gene transfer procedure. Examples of such procedures include, but are not limited to, RNA viral mediated gene transfer such as retroviral transduction, DNA viral mediated gene transfer, electroporation, calcium phosphate mediated transfection, microinjection, or liposome mediated gene transfer. The type of procedure required to achieve an engineered cell that secretes the desired gene product will depend on the nature and properties of the cell. The specific technology for introducing such genes into such cells is generally known and well within the skill of the art.

In particular embodiments, gene therapy was used to halt or ameliorate EAE disease in SJL/J mice, which is analogous to MS in humans, wherein continuous exposure to low levels of PLP antigen in the absence of a co-stimulatory signal—conditions rendering T cells unresponsive—resulted in a striking abrogation of both clinical and histological signs of disease. To provide this therapeutic antigen-specific signal, mice suffering from EAE were injected, after the initial acute attack, with syngeneic diploid fibroblast cells transduced with a retroviral vector designed to encode PLP 101-157 targeted for secretion. This protocol delivered a low-level, constant exposure to antigen which showed no anaphylactic response as seen in some cases upon repeated injection of antigen. [Pedotti, R., et al., Nat. Immunol., 2: 216-222 (2001).]

In other studies, cells have been transduced with a retroviral vector designed to encode a second epitope antigen, MBP amino acids 89-101. [Sakai, K., et al., J. Neuroimmunol., 19: 21-32 (1988).] This is important since T cells responding to this epitope have been detected in many MS patients. [Zhang, J., et al., J. Exp. Med., 179: 973-984 (1994); Martin, R., et al., J. Immunol., 145: 540-548 (1990); Ota, K., et al., Nature, 346: 183-187 (1990); Pelfrey, C. M. et al., J. Immunol., 165: 1641-1651(2000); Tejada-Simon, M. V., Hong, J., Rivera, V. M., Zhang, J. Z., Eur. J. Immunol. 31: 907-917 (2001).]

A second epitope, MBP 89-101 (SEQ ID NO.: 17) was examined. See FIG. 14. By inducing disease with MBP protein (instead of MSCH) the disease is ameliorated using transduced fibroblasts secreting either the MBP 89-101 (SEQ ID NO.: 17) or PLP 139-151 (SEQ ID NO.: 4) epitope. In one embodiment, the PLP-secreting fibroblasts are able to protect MBP-induced EAE mice against relapse by silencing PLP-specific T cells. In another embodiment, mice receiving the MBP-secreting fibroblasts, however, were also protected from relapse despite the fact that the MBP 89-101 epitope is less encephalogenic than is PLP 139-151. Thus, the secretion of only one epitope can result in the control of disease despite the fact that pathogenic T cells of other specificities are present in sick animals.

In another embodiment of the invention, increases in IL-2- and INF-γ-expressing T cells were found in the brains of the untreated EAE mice at the time of the first relapse. This contrasts with mice treated with PLP-secreting fibroblasts which do not relapse and possess T cells generating anti-inflammatory cytokines such as IL-4 and IL-10. Thus, both PLP- and MBP-secreting fibroblasts can treat MBP-induced EAE since the antigen-specific therapy acts through a cytokine-induced pathway. In yet another embodiment, successful use of a chamber to sequester the transduced cells demonstrated that host T-cell/transduced cell contact was not required. A non-limiting example of a chamber includes the TheraCyte 4.5 microliters (μl) immunoisolation device (TheraCyte, Irvine, Calif.). Other chambers may be used as known to those skilled in the art. Although the mechanism is not necessary for enablement of the invention, the secreted mini-protein may be presented on the MHC class II molecules of antigen presenting cells in the absence of co-stimulation, thereby inducing regulatory or suppressor T cells mediated by anti-inflammatory cytokines. [von Herrath, M. G., Harrison, L. C., Nat. Rev. Immunol. 3: 223-232 (2003).]

In a particular embodiment, no exacerbation of disease was observed upon treatment with transduced fibroblasts. In this embodiment, the transduced cells were confined within a chamber that was implanted subcutaneously which could also be removed surgically. Human studies utilizing these chambers have shown that parathyroid tissue was successfully sequestered for over a year. [Yanay, O., et al., Hum. Gene Ther. 14: 1587-1593 (2003).] In rats, cells transduced with an erythropoietin vector and confined in these chambers express the transgenic protein for more than 12 months. [Yanay, O., et al., Hum. Gene Ther., 14: 1587-1593 (2003).] In an embodiment of the present invention, long-term expression of a reporter gene by transduced cells was observed in murine implants. In another embodiment, histological examination of these chambers, 42 days after implantation, revealed a high degree of vascularization suggesting that the therapeutic mini-protein can be secreted for long periods of time. In addition, there was no evidence of immune cell infiltrate around the device that could potentially exacerbate autoimmunity. In a particular embodiment, allogeneic transduced cells were used, which greatly the enhanced the practicality of this protocol since one "universal" allogeneic cell line can be used to treat patients with diverse MHC haplotypes without the possibility of rejection.

An aspect of the present invention effected silencing of specific T cells using an MBP epitope as well as the PLP epitope; both are epitopes which are recognized by T cells of many patients with the DR2 haplotype. [Ota, K., et al., Nature, 346: 183-187 (1990); Tejada-Simon, M. V., Hong J, Rivera, V. M., Zhang, J. Z., Eur. J. Immunol. 31: 907-917

(2001); Chou, Y. K., et al., J. Neuroimmunol., 38: 105-113 (1992); Correale, J., et al., Neurology, 45: 1370-1378 (1995); Trotter, J. L., et al., J. Neuroimmunol., 84: 172-178 (1998).] In particular embodiments, EAE was successfully treated, without the requirement that all epitopes recognized by pathogenic T cells be secreted. The treatment of MS patients need not be individualized despite extensive, though more limited as compared to the general population, MHC polymorphism and epitope diversity. In further embodiments, wherein initial screening of the myelin-specific T cell reactivities of the patient indicate that expression of epitopes other than MBP 89-101 and PLP 139-151 may be more efficacious, the present invention provides mini-gene constructs which is designed as a cassette to facilitate exchange of epitope sequences.

In summary, therefore, as well as addressing practical and safety issues, not all encephalogenic epitopes need to be secreted to silence pathogenic T cells and treat disease.

Definitions:

As used herein a "patient" is any mammalian animal which has T cells as part of its immune system including, but not limited to, human, dog, cat, mouse, rat, gerbil, hamster, guinea pig, sheep, cow, goat, rabbit, monkey, chimpanzee, pig, dolphin, and horse.

As used herein an "epitope" is the simplest form of an antigenic determinant, on a complex antigenic molecule, which can interact with an antibody or T cell receptor. Examples of complex antigenic molecules include, but are not limited to: PLP, MBP, MOG, acetylcholine receptor, TSH receptor, insulin, and collagen.

As used herein a "domain" is a region of a protein having some distinctive physical feature or immunological role.

As used herein "allogeneic" refers to cells, tissues, or individuals that are of the same species, but are antigenically distinct because genes at one or more loci are not identical in sequence.

As used herein a "gene" is a deoxyribonucleotide sequence coding for an amino acid sequence.

As used herein a "mini-gene" is a deoxyribonucleotide sequence coding for an mini-protein.

As used herein a "mini-protein" is any expressed antigenic protein sharing homology, regardless of size or region, with the full antigenic protein.

As used herein, the term "engineered" is intended to refer to a cell into which has been introduced one or more recombinant genes such as, but not limited to, a gene encoding an epitope of a self antigen.

As used herein, the term "vector" is used in reference to nucleic acid molecules that transfer DNA or RNA segment(s) from one cell to another. Retroviral vectors transfer RNA, which is then reverse transcribed into DNA. It is not intended, however, that the present invention be limited to retroviral or any other specific class of vector.

The term "expression vector" as used herein refers to a recombinant molecule containing a desired coding sequence and appropriate nucleic acid sequences necessary for the expression of the operably linked coding sequence in a particular host organism. Eukaryotic cells are known to utilize promoters, enhancers, and termination and polyadenylation signals.

The terms "promoter element" and "promoter" as used herein, refer to a DNA sequence that precedes a gene in a DNA polymer and provides a site for initiation of the transcription of the gene into mRNA.

The term "operably linked" as used herein refers to the linkage of nucleic acid sequences to produce a nucleic acid molecule that is capable of directing the transcription of a given gene and/or the translation to a desired protein molecule. The term also refers to the linkage of amino acid sequences to produce a functional protein.

As used herein, the term "selectable marker" refers to the use of a gene which encodes an enzymatic activity that confers resistance to an antibiotic or drug upon the cell in which the selectable marker is expressed. Selectable markers may be "dominant;" a dominant selectable marker encodes an enzymatic activity which can be detected in any eukaryotic cell line. Non-limiting examples of dominant selectable markers include the bacterial aminoglycoside 3' phosphotransferase gene (also referred to as the neo gene) which confers resistance to the drug G418 in mammalian cells; the bsr gene which permits blastocidin-S resistance; the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that there use must be in conjunction with a cell line that lacks the relevant enzyme activity. Non-limiting examples of non-dominant selectable markers include the thymidine kinase (tk) gene that is used in conjunction with tk7 cell lines, the CAD gene that is used in conjunction with CAD-deficient cells and the mammalian hypoxanthine-guanine phosphoribosyl transferase (hprt) gene that is used in conjunction with hprt cell lines. A review of the use of selectable markers in mammalian cell lines is provided in Sambrook, J., et al., Molecular Cloning: A Laboratory Manual, 2nd ed., Cold Spring Harbor Laboratory Press, New York (1989) pp. 16.9-16.15.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection in methods which depend upon binding between nucleic acids.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method As used herein, the term "polymerase chain reaction" ("PCR") refers to the methods of U.S. Pat. Nos. 4,683,195, 4,683,202, and 4,965,188, all of which are hereby incorporated by reference, directed to methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are considered to be "PCR amplified."

As used herein, the terms "restriction endonucleases" and "restriction enzymes" refer to enzymes that cut double-stranded DNA at or near a specific nucleotide sequence.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" or "nucleic acid sequence encoding an amino acid sequence" means a DNA sequence comprising the coding region of a gene or in other words the DNA sequence which encodes a gene product. The coding region may be present in either a cDNA or genomic DNA form. Suitable control elements such as enhancers/promoters, splice junctions, polyadenylation signals, etc. may be placed in close proximity to the coding region of the gene if needed to permit proper initiation of transcription and/or correct processing of the primary RNA transcript.

The examples which follow illustrate the design and construction of a portion of the PLP gene and the MBP gene, in vitro and in vivo expression of the PLP gene and MBP gene, the in vivo effects of the PLP gene and MBP products, the use of the PLP and MBP products to treat EAE—which is analogous to treatment of MS in humans—genetic modifications to the PLP and MBP products to improve efficacy, the expression PLP and MBP genes in allogeneic cells, and the use of these allogeneic cells in an implantable chamber.

The following examples are presented to illustrate the invention, and are not intended to limit the scope thereof.

EXAMPLE 1

Design and Construction of the PLP Gene

In SJL/J mice, the encephalogenic epitope of PLP comprises amino acids 139-151. [Takahashi, N., et al., Cell, 42:139-148 (1985); Sakai, K., et al., J. Neuroimmunol., 19:21-32 (1988); Kono, D. H., et al., J. Exp. Med., 168:213-227 (1998).] The vector is designed such that the gene product encoded by it is constitutively secreted from mammalian cells, such as, but not limited to fibroblasts, stem cells, peripheral blood monocytes, and lymphocytes. Since the complete PLP protein is a hydrophobic transmembrane protein [Diehl, H-J.,et al, PNAS U.S.A., 83:9807-9811 (1986)], with the encephalogenic epitope being extracellular, a plasmid encoding amino acids 101-157 and additional amino acids required for secretion was constructed. See FIG. 1, SEQ ID NOs.: 1-6. This sequence is hydrophilic in character.

1. Oligonucleotide Synthesis and Construction of the PLP pRc/CMV Vector

Oligonucleotides can be synthesized manually, e.g., by the phospho-tri-ester method, as disclosed, for example in [Letsinger, R. L., et al., J. Am. Chem. Soc., 98:3655 (1967)], the disclosure of which is incorporated by reference. Other methods are well known in the art. See also [Matteucci and Caruthers, J. Am. Chem. Soc., 103:3185 (1981), the disclosure of which is incorporated by reference.

Preferably, however, the desired gene sequence can be made by automated synthesis of individual oligonucleotides at 0.2 µM concentrations. For PLP amino acids 101-157 (see FIG. 1, SEQ ID NOs. 3) DNA syntheses were performed on a Perkin Elmer/Applied Biosystems Division Model 394 DNA synthesizer using cyanoethyl-protected phosphoramidites. The dimethoxytrityl (DMT) group was not removed from the 5'hydroxyl group to allow for purification. After normal cleavage from the resin using concentrated ammonium hydroxide and deprotection at 55° C. for 16 hours, the oligonucleotides were purified using oligonucleotide purification cartridges (OPC) according to the manufacturer's instructions (Applied Biosystems Inc.) Five oligonucleotides of the following sequences were synthesized:

```
OLG 1
5' CGGCGACTACAAGACCACCATCTGCGGCAAG  (SEQ ID NO: 18)
GGCCTGAGCGCAACGGTAACAGGGGGCCAGAAGG
GGAGGGGTTCCAG AGGCCAACATCAAGCTCATT
CTCTCGAGC-3',

OLG 2
5' GAGCTTGATGTTGGCCTCTGGAACCCCTCCC  (SEQ ID NO: 19)
CTTCTGGCCCCCTGTTACCGTTGCGCTCAGGCCC
```

```
                                      -continued
TTGCCGCAGATGGTGGTCTTGTAGTCGCCGGGC
C-3', OLG 3
5' GGGTGTGTCATTGTTTGGGAAAATGGCTAGG   (SEQ ID NO: 20)
ACATCCCGACAAGTTTGTGGGCATCACCTATGCT
AGCCTTAAGTAGGATCCTTGAATAGGTA-3', OLG 4
5' AGCTTACCTATTCAAGGATCCTACTTAAGGC   (SEQ ID NO: 21)
TAGCATAGGTGATGCCCA-3',
and OLG 5
5' CAAACTTGTCGGGATGTCCTAGCCATTTTCC   (SEQ ID NO: 22)
CAAACAATGACACACCCGCTCGAGAGAAT-3',.
```

Each purified oligonucleotide was dried under vacuum, washed with 1 ml of sterile double distilled water and then concentrated to dryness under vacuum (Speed vac evaporator; Savant Inc.). 80 pM of each oligomer was kinased at 37° C. for 1 hour by resuspending in 55.6 μl of 1× kinase buffer (Polynucleotide Kinase Buffer; Boehringer Mannheim, Indianapolis, Ind.) containing 10 units of polynucleotide kinase (Boehringer Mannheim) and 100 μM of ATP. The individual oligonucleotides were combined in the presence of 2×SSC (0.03M Sodium Citrate, p7.0, and 0.3M NaCl) in a PCR tube with their respective complementary oligomer partners for annealing. Each annealed set measured 200 μl in volume. Oligomer OLG1 (SEQ ID No. 18) was annealed with OLG2, (SEQ ID NO.: 19) and oligomers OLG4 (SEQ ID NO.: 21) and OLG5 (SEQ ID NO.: 22) were annealed with OLG3 (SEQ ID NO.: 23). Annealing was performed in a Perkin-Elmer 9600 Thermocycler, programmed as follows: 1) 99.9° C. for 2 minutes, and 2) 99.9° C. to 4° C. in 15 minutes. During the temperat descent to 4° C., when the thermocycler temperature reached 37° C., the solution containing the oligomer duplex OLG1 (SEQ ID NO.: 18) and OLG2 (SEQ ID NO.: 19) was combined with the solution containing the oligomers OLG3 (SEQ ID NO.: 20), OLG4 (SEQ ID NO.: 21), and OLG5 (SEQ ID NO.: 22). The descent cycle was then continued until it reached 22° C. Subsequently, 5 units (5 μl) of T4 ligase (Boehringer Mannheim, Indianapolis, Ind.) and 45 μl of manufacturer's 10× T4 DNA ligation buffer (Boehinger Mannheim, Indianapolis, Ind.) was added, and ligation proceeded overnight at 10° C.

The ligated DNA was precipitated with 2 volumes of 100% ethanol and incubated at −70° C. for 1 hour. The precipitate was centrifuged for 30 minutes at 17000×g at 4° C. The supernatant was discarded and pellet was washed with 1 ml of 70% ethanol and centrifuged for 10 minutes at 17000×g at 4° C. The DNA pellet was dried under vacuum (Speed vac evaporator; Savant Inc.) and resuspended in 45 μl sterile double distilled water.

DNA of the correct molecular weight was isolated by electrophoresis. 5 μl of 10× loading buffer (6.25 g Ficoll and 0.93 g Disodium EDTA/25 ml 10% SDS, Orange G, Xylene Cyanole, and Bromophenol Blue) was added to the sample and loaded onto a 14.5 cm×16 cm×0.15 mm urea/acrylamide gel (7M urea/8% acrylamide with 1.1% Bis). TBE (89 mM Tris, 89 mM Boric acid, and 2 mM EDTA pH8.0) was used as both gel and electrophoresis buffer. The sample was electrophoresed at 35 mA until the Orange G dye line had migrated within 1 cm of the bottom of the gel. The acrylamide gel was washed twice with water for 5 minutes. After the last wash, the gel was incubated for 3 minutes in a 500 ml solution containing 10 μl of 10 mg/ml of ethidium bromide, and visualized under a UV-light source. The band corresponding to the ligated DNA was excised and cut into small pieces for electroelution in an IBI electroelutor apparatus (Model UEA: International Biotechnologies Inc., New Haven, Conn.).

For electroelution, the salt trap of the apparatus was filled with 125 μl of 7M sodium acetate/bromophenol blue dye solution. The buffer chamber was filled with ½× TBE. The sample was electroeluted for 1 hour at 85V. After removing the eluted DNA, the sample well was washed with ½× TBE and combined with the initial eluate. The eluted DNA was then precipitated overnight at −70° C. with 2 volumes of 100% ethanol. The precipitate was pelleted, washed as previously described, and resuspended in 15 ul of sterile double distilled water.

Preceding the ligation of the eluted partial PLP gene to the pRc/CMV vector (Invitrogen, San Diego, Calif.), the pRc/CMV vector construct was cut with the restriction endonucleases Apa I and Hind III according to the Manufacturer's instructions (Boehringer Mannheim, Indianapolis, Ind.). The resuspended PLP gene construct was then added to a 5 μl mixture containing 0.3 μg of pRc/CMV cut vector (2 μl), 1 unit T4 ligase (1 μl) (Boehringer Mannheim, Indianapolis, Ind.), and 2 μl of Manufacturer's 10× T4 DNA ligation buffer (Boehringer Mannheim, Indianapolis, Ind.). The ligated vector was then transformed into the competent cell line AG1.

Transformation proceeded by combining the ligation mixture with the AG1 cells and incubating it on ice for 20 minutes. The cell/vector mixture was then incubated at 42° for 2 minutes and plated overnight onto a Luria Broth agar (LB; Bio101, Vista, Calif.) plate, supplemented with 80 mg/ml of ampicillin (Sigma, St. Louis Mo.). Colonies were screened for the correct sequence vector by first isolating the plasmid DNA and then sequencing the DNA.

To isolate the plasmid, a commercially available plasmid purification kit, Wizard Minipreps (Promega, Madison, Wis.) was used. Colonies were picked from the LB/Amp plates and grown for 3.5 hours in 5 ml of LB medium (BIO 101, Vista, Calif.) supplemented with 80 mg/ml of ampicillin (Sigma, St. Louis, Mo.). 3 ml of the medium was centrifuged at 17000×g at room temperature, for 1 minute to pellet the cells. Isolation of the plasmid proceeded according to the Manufacturer's instructions. 1 μg of the isolated DNA was used for sequencing.

The oligonucleotide sequence can be checked by methods well known in the art, such as that described by [Sanger et. al., PNAS U.S.A. 70:1209 (1973)] or by the Maxam-Gilbert method, [Meth. Enzymology, 65:499 (1977)], the disclosures of both of which are incorporated herein by reference. Preferably, the plasmid can be sequenced using an automated DNA sequencer. For the PLP pRc/CMV construct, the plasmid was sequenced using automated fluorescent DNA sequencing procedures (Perkin Elmer/Applied Biosystems Inc, Foster City, Calif.) using the following primers:

```
GATTTAGGTGACACTATAG,       (SEQ ID NO: 23)
and

TAATACGACTCACTATAGGG.      (SEQ ID NO: 24)
```

Figure 1:
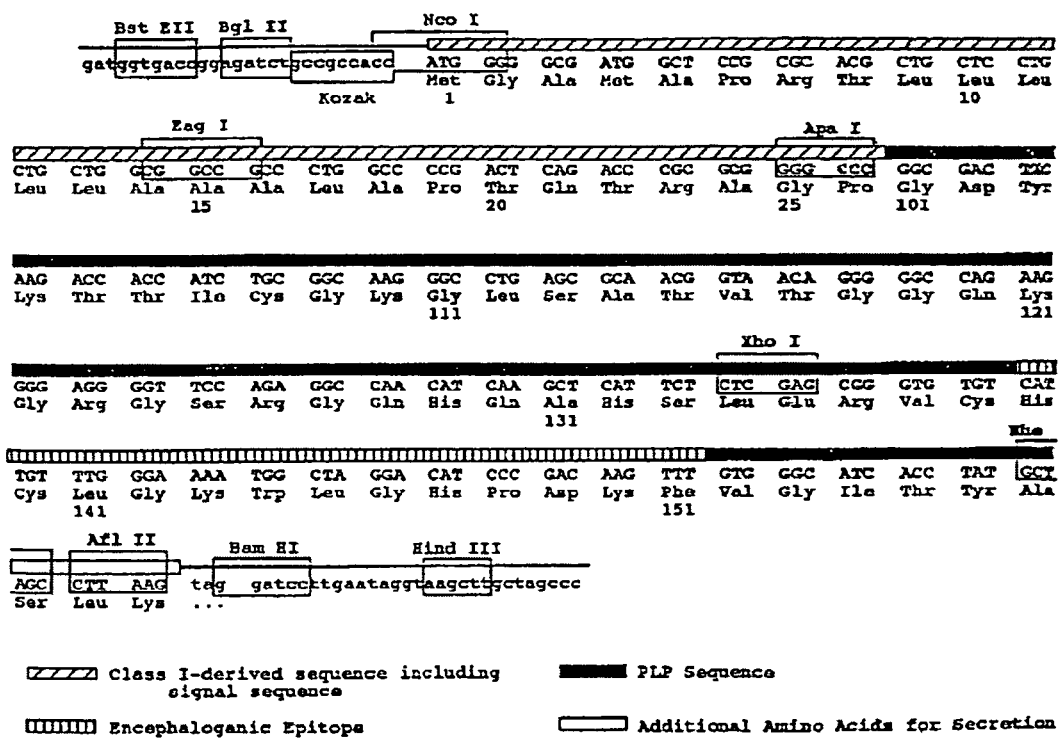
FIG. 1 is a map showing a construct having a nucleotide sequence corresponding to SEQ ID NO: 31 and encoding a polypeptide having an amino acid sequence corresponding to SEQ ID NO: 32. The construct encodes a partial PLP gene product, amino acids 101-157, corresponding to SEQ ID NO: 3.

These primers primed off the vector, which flanked the Kozak and "stop" site of the total construct. FIG. 1 shows a map of the partial PLP gene showing the sequence of the gene product and restriction sites. At the 5' end of the construct a hydrophobic leader sequence from the MHC class I H2-L$^2$ gene (SEQ ID NO.: 2) was inserted to enable the gene product to be synthesized in the endoplasmic reticulum (ER) for later constitutive secretion. [Linsk, R., et al., J. Exp. Med., 164: 794-813 (1986).] In addition, a lysine codon at the 3' end was added to ensure that the protein could not be retained in membrane. A Kozak box was included in the construct to ensure efficient translation. Restriction sites Afl II and BamHI were included in the construct to allow for insertion of further epitopes.

Similarly, additional vectors were also constructed for different amino acid sequences such as MBP amino acids 71-111 (see FIG. 14, SEQ ID NO.: 10) and with different leader sequences chemokine signal sequence (SEQ ID NO.: 9) with PLP amino acids 101-157 (SEQ ID NO.: 3) (see FIG. 21), as well as with different restriction sites (see FIGS. 1, 14, and 21) (SEQ ID NOs.: 1, 6, 8, 13, 14, 16.)

EXAMPLE 2

In Vitro Expression of the PLP Protein

The following experiments were performed in order to demonstrate that the PLP vector encodes a protein which is constitutively secreted. Specifically, the mRNA levels of PLP were evaluated in SJL fibroblast cells transfected with the pRc/CMV-PLP vector, and mRNA and protein levels of PLP were evaluated in SJL fibroblast cells transfected with the pGlPLPSvNa vector.

1. Establishment of Fibroblast Cultures

Syngeneic fibroblasts (derived from SJL mice) were obtained from Dr. G. Dreskler (Uniformed Services University, Bethesda, Md.) and expanded at 37° C. incubation using DMEM growth medium, supplemented with 5% glutamine and 10% FCS. The cells were harvested and frozen at $1\times10^7$ cells per vial, and aliquots were quality control tested for mycoplasma, sterility and viability.

2. Retroviral Constructs

Figure 2:
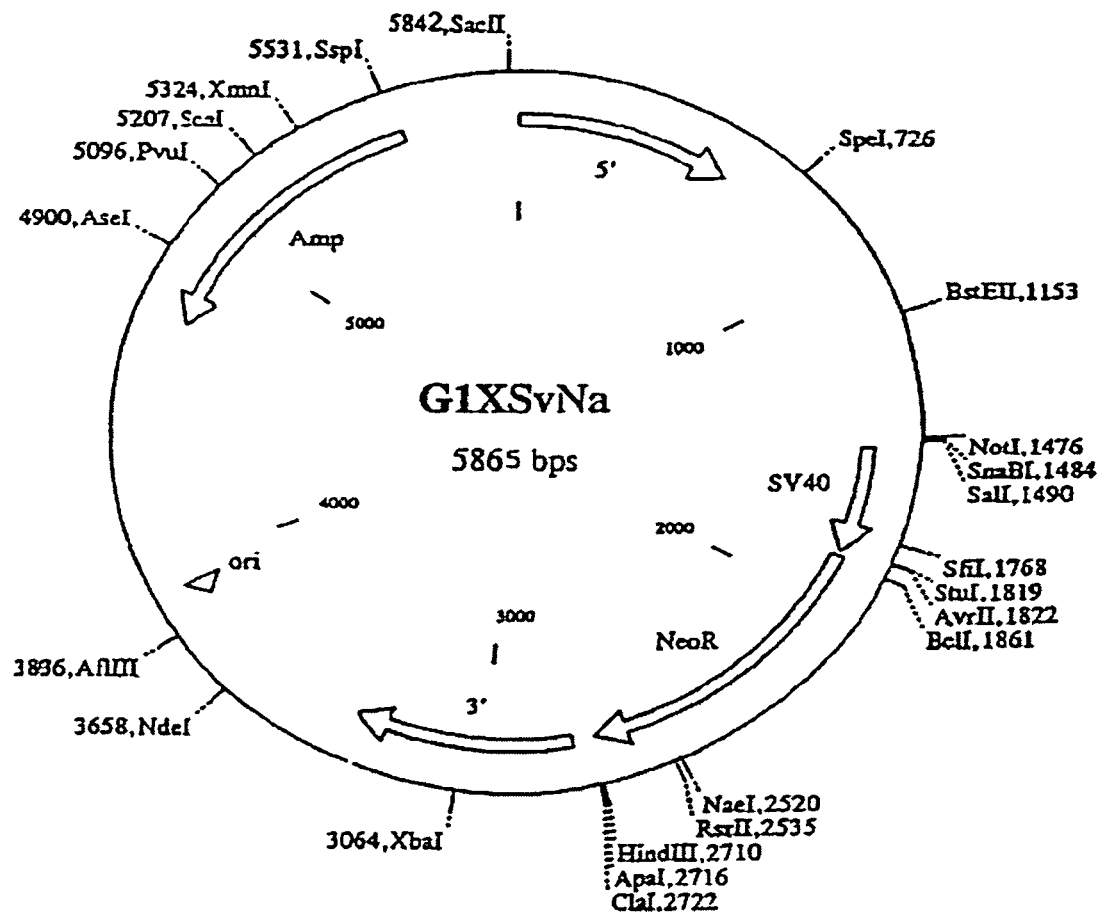
FIG. 2 is a map of the GlXsvNa (SEQ ID NO.: 7) vector illustrating restriction sites and functional features.
Figure 3:
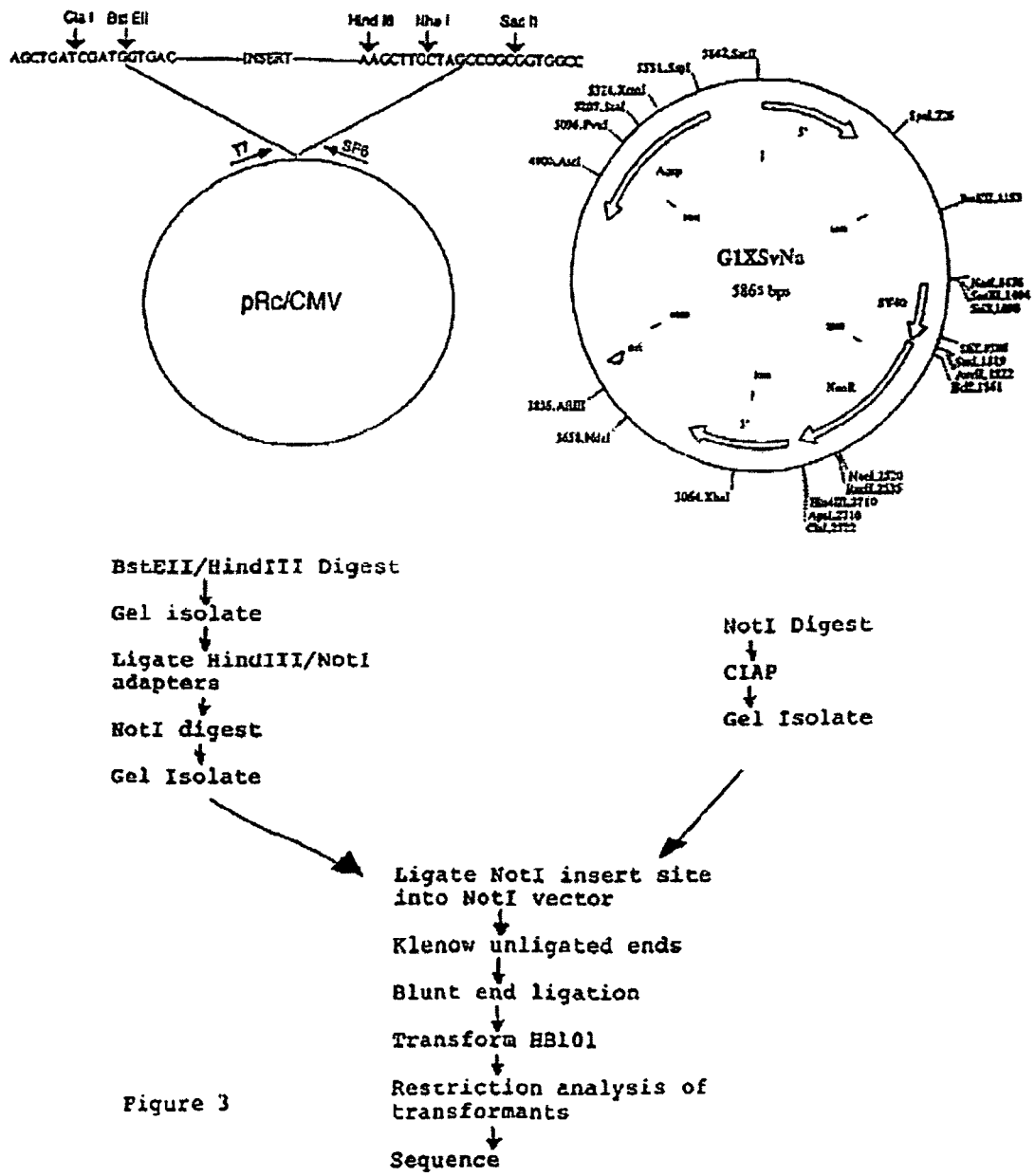
FIG. 3 outlines the method of constructing a GlXSvNa vector containing the PLP gene insert.

A recombinant retroviral vector in which exogenous genes are inserted into a retroviral vector was constructed. The cloning strategy was to construct a pGlXSvNa vector (W. French Anderson, University of Southern California) containing the PLP insert from pRc/CMV-PLP. The pGlXSvNa vector, like most retroviral vectors used in preclinical and clinical trials, is derived from the Moloney murine leukemia retrovirus (Mo-MLV). [Rosenberg, S. A., et al., N. Eng. J. Med., 323:570-578 (1990), Culver, K. W., et al., Science, 256:1550-1552 (1992).] The GlXSvNa vector is a 5865 bp vector whose map, functional features and complete DNA sequence are shown in FIG. 2. FIG. 3 illustrates the procedure for constructing the pGlPLPSvNa vector. Essentially, the pRc/CMV-PLP vector was digested with BstEII/HindIII and PLP encoding fragment was isolated by gel electrophoresis. After electroelution, HinduIII/NotI adapters (Stratagene, La Jolla, Calif.) were ligated into the HindIII site of the eluted fragment. A NotI digestion was performed to generate NotI ends. A NotI digest was performed on pGlXSvNa and the 5865 bp fragment was isolated, electroeluted, and a CIAP (Calf intestine alkaline phosphatase treatment) was performed on the fragment ends. The NotI site of the insert was ligated into the NotI site of the vector. BstEII ends of the insert and NotI site of the vector were Klenowed. A blunt end ligation is performed to close the vector. HB101 cells were transformed with ligation mix and restriction analysis was performed to determine which vectors contain insert and the insert orientation. The recombinant retroviruses are non-replicating and incapable of producing infectious virus.

3. Retroviral Vector Supernatant

To prepare supernatant containing PLP-recombinant retrovirus, the PLP-transduced retroviral packaging cell line PA317 was grown in 4 ml of appropriate culture medium in a T25 flask (Coming, Cambridge, Mass. Retroviral vector supernatant was produced by harvesting the cell culture medium when cells were 80-90% confluent, and stored in 1 ml aliquots at −70° C.

The following tests are performed on the PLP cell line and/or the vector supernatants:
(1) The viral titer is determined using 3T3 cells. Viral preparations with titers greater than $5\times10^4$ colony forming units/ml were used.
(2) Sterility of the producer cell line and the supernatant is assured by testing for aerobic and anaerobic bacteria, fungus and mycoplasma.

The PLP-vector preparations from PA317 are extensively tested to assure that no detectable replication competent virus is present. This is particularly relevant to the embodiment of the invention wherein the invention is used to treat humans. Tests on both the viral supernatant and on the transduced fibroblasts are performed to determine if there is replication competent virus present. The following tests are performed on the producer cell line and/or the viral supernatant:
(1) The viral titer is determined using 3T3 cells. Viral preparations with titers greater than $5\times10^4$ colony forming units/ml is used.
(2) Southern blots are run on the producer cell line to detect the partial PLP gene.
(3) PLP production by the producer cell line is measured and should be significantly above baseline control values, as determined by ELISA assay.
(4) Sterility of the producer cell line and the supernatant is assured by testing for aerobic and anaerobic bacteria, fungus and mycoplasma.
(5) Viral testing is performed including: MAP test, LCM virus, thymic agent, S+L-assay for ecotropic virus, S+L assay for xenotropic virus, S+L-assay for amphotropic virus and 3T3 amplification.
(6) Electron microscopy is performed to assure the absence of adventitious agents.

Following the introduction of the gene into fibroblasts, the following tests are performed on the fibroblasts prior to administration to patients.
(1) Cell viability is greater than 70% as tested by trypan blue dye exclusion.
(2) Cytologic analysis is performed on over 200 cells prior to infusion to assure that tumor cells are absent.
(3) Sterility is assured by testing for aerobic and anaerobic bacteria, fungus and mycoplasma.
(4) S+L-assay including 3T3 amplification must be negative.
(5) PCR assay for the absence of 4070A envelope gene must be negative.
(6) Reverse transcriptase assay must be negative.
(7) Southern blots run on the transduced fibroblasts to assure that intact provirus is present.
(8) PLP protein assay to assure the production of PLP protein.

As an alternative, one skilled in the art could also employ the National Vector Laboratory to ascertain whether there is an absence of infectious particles. These protocols are well known in the art and follow FDA guidelines.

4. Transfection of Fibroblasts

Prior to the transfection of the SJL fibroblasts, highly purified PLP-pRc/CMV vector was isolated from the transformed AG1 cells. Large scale purification was performed by using a commercially available kit and CsCl gradient banding. Initial purification was accomplished using a Wizard Megaprep Kit (Promega, Madison, Wis.). A 1000 ml culture of transformed AG1 cells, grown overnight in LB/Amp at 37° C., was pelleted and the plasmid DNA isolated according to the Manufacturer's instructions. The isolated DNA, which was suspended in 3 ml of TE buffer (10 mM Tris-HCl, pH 7.4, and 1 mM disodium EDTA, pH, 8.0) was further processed by CsCl gradient banding. A modified CsCl banding of the DNA was performed based on procedures found in "Current Protocols in Molecular Biology, Vol 1" (Greene Publishing Associates and Wiley-Interscience).

After the DNA band was extracted from the ultracentrifuge tubes, ethidium bromide was removed from the sample by washing it with 3 volumes of SSC saturated isopropanol. The wash was repeated until the aqueous layer appeared clear. CsCl was removed by precipitation. Two volumes of 0.2M NaCl/TE and 2 volumes of 100% ethanol (relative to the combined total volume of DNA solution and 0.2M NaCl/TE) were added to the sample, mixed and placed on ice for 10 minutes. The precipitated DNA was pelleted by centrifugation at 10000×g for 10 minutes at 4° C. The pellet was washed with cold 70% ethanol, recentrifuged at 10000×g for 10 minutes at 4° C., and dried under vacuum (Speed vac evaporator; Savant Inc.). The purified DNA was resuspended with double-distilled sterile water and utilized in the transfection process.

Test SJL fibroblasts were transfected using LipofectAMINE Reagent (Life Technologies Inc./Gibco BRL) according to the manufacturer's instructions. Control SJL fibroblasts underwent the same procedure without the presence of a DNA construct. Three jig of CsCl purified PLP-pRc/CMV plasmid and 25 µl of Lipofectamine were used for transfection. Approximately $3\times10^5$ SJL cells, seeded overnight into 25 cm² culture flasks (Corning Costar Corp., Cambridge, Mass.) and grown at 37° with 5% $CO_2$ in 5 ml of DMEM culture medium (Dulbecco's Modified Eagle's Medium (Irvine Scientific, Santa Ana, Calif.), supplemented with 5% glutamine, 10% Fetal Calf Serum, 25 Units/ml of penicillin G sodium, and 25 µg/ml of streptomycin sulfate, were washed with 3 ml serum free HL-1 medium (Hycor Biomedical Inc., Irvine, Calif.). After the DNA/lipofectamine complexes were incubated with cells for 6 hours at 37° with 5% $CO_2$, 1 ml of DMEM was added to the flasks. The flasks were incubated overnight at 37° C. with 5% $CO_2$. The medium was replaced with 5 ml of fresh DMEM the next morning. Thirty six hours after the end of the transfection period, the medium was replaced with 5 ml of DMEM containing 900 µg of G418 (Life Technologies Inc./Gibco BRL)/ml of medium. The test cells were grown in the presence of 900 µg of G418 of medium until all the control cells had died; and no more cell death could be observed in the test sample flask. The G418 concentration was then reduced to 600 µg/ml of culture medium for duration of cell culturing procedures.

5. Transduction of Fibroblasts

Retroviral constructs containing a neo-selectable marker together with either the PLP gene or the LacZ gene were used to transduce fibroblasts. Transduction with the retrovirus was performed on healthy cells (90% viable, as determined by trypan blue staining) $2\times10^6$ cells were plated in 0.5 ml DMEM-10 media (DMEM media supplemented with 10% fetal calf serum, 2 mM L-glutamine, 50 U/ml penicillin G, 50 mg/ml streptomycin in one well of a 24-well plate (Falcon, Franklin Lakes, N.J.). Cells were placed in the incubator and allowed, to settle (37° C., 5% $CO_2$). After cells had settled, 1 ml of retroviral supernatant and polybrene (Sigma, St. Louis, Mo.) (final concentration 10 µg/ml) was added to the well. Cells were incubated as above for 2.5 hours without shaking. After 2.5 hours, cells were transferred to a T25 flask and DMEM-10 media was added to a total volume of 8 ml. Selection media (culture media comprising DMEM-10 supplemented with 900 µg/ml G418 (Gibco, Grand Island, N.Y.) was added on the third day after transduction. The G418 concentration was then reduced to 600 µg/ml of culture medium for the duration of cell culturing procedures.

6. mRNA Expression Analysis mRNA isolation was performed using aseptic techniques, RNAse free supplies, and DEPC (Diethylpyrocarbonate) treated solutions. $4\times10^6$ experimental and control SJL cells were washed twice with cold Phosphate-buffered saline, resuspended in 200 µl cell lysis mix (10 mM TRIS pH 7.5, 0.15M NaCl, 1.5 mM $MgCl_2$, 0.65% NP 40), vortexed, and centrifuged at 17000×g at 4° for 5 minutes. The supernatant was transferred to a tube containing 200 µl of urea mix (7M urea, 1% SDS, 0.35M NaCl, 10 mM EDTA, and 10 mM Tris-HCL, pH 7.5) and 400 µl of phenol:chloroform:isoamyl alcohol (25:24:1). The solution was vortexed and centrifuged for 1 minute at 17000×g. This procedure was repeated twice using the aqueous layer and then transferred to a tube containing 400 µl of phenol and washed as before. The aqueous layer was transferred again to another tube, and precipitated with 1 ml of 100% ethanol overnight at −20° C. The precipitated RNA was washed with 1 ml 70% ethanol. After the ethanol was discarded, the pellet was dried under vacuum. One µg of the RNA was used for RT-PCR analysis.

RT-PCR was performed using a commercially available kit, GeneAmp RNA PCR Kit (Perkin Elmer/ABI) according to the Manufacturer's instructions. The following primers were used to amplify the cDNA:

```
5'-GCGACTACAAGACCACCATCT-3',    (SEQ ID NO: 25)
and

5'-TAAGGCTAGCATAGGTGATG-3'.     (SEQ ID NO: 26)
```

The PCR products were electrophoresed on a 1.5% agarose (SeaKem GTG; PMC)/TAB gel with 1 µl of 10 mg/ml of ethidium bromide/ml of agarose solution. The gel was electrophoresed using TAE buffer at a constant 40 mA. Electrophoresis was continued until the molecular weight marker bands had separated adequately enough, to verify the PCR products approximate molecular size. The DNA band of interest was then excised and gel purified, using the commercially available MERmaid Kit (Bio 101, Vista, Calif.), according to the Manufacturer's instructions. The purified DNA was then sequenced by automated Fluorescent DNA sequencing procedures (Perkin Elmer/ABI, Foster City, Calif.).

FIG. 4 is an agarose gel showing PLP-specific RT-PCR products. The data illustrates that mRNA is present in both PLP-transduced and PLP-transfected cells. The correlation between mRNA and secreted protein remains to be determined since peptide concentration does not necessarily correspond to the level of mRNA.

7. Protein Expression Analysis

The in vitro qualitative expression of the proteins encoded by the PLP gene was detected immunologically by ELISA. Undiluted supernatants from cultures of fibroblasts transduced with the PLP gene were tested. Wells of 96 microtiter plate were coated with the supernatants. Primary anti-PLP-antibody 4E10 139-151, from Dr. M. Lees (Harvard University), is specific for PLP 139-151 and was added to wells as undiluted hybridoma supernatant followed by horseradish peroxidase (HRP)—conjugated goat anti-mouse secondary antibody in a concentration of 1:500. The plate was developed and analyzed at 490 nm on a microplate reader. FIG. 5 illustrates the results of ELISA assays on transduced fibroblast supernatants. Samples 1 and 2 were PLP (amino acids 139-151) and HIV gp120 peptides used at a concentration of 5 ug/ml. This experiment illustrates that the transduced PLP-transduced fibroblasts do produce and secrete the partial PLP protein.

EXAMPLE 3

In Vitro Effects of the PLP Protein

Critical to the success of this invention in the embodiment of this example is the ability to deliver genetically manipulated fibroblasts to patients so that the cells survive in sufficient numbers and for long periods of time, in order that continuous secreted antigen may be provided to the patient.

To assess the fate of transplanted transduced fibroblasts, SJL fibroblasts transduced with retrovirus encoding B-galactosidase were injected subcutaneously between the shoulders of SJL mice. All mice were female mice of the SJL strain between 6-8 weeks old and were obtained from Jackson Labs. Animals were housed and maintained according to NIH guidelines (National Research Council, 1986). These fibroblasts survived in large numbers after 60 days. Fibroblasts injected into the footpad or intramuscularly could not be detected at eight days.

1. In Vivo Fate B-gal Transduced Cells

The activity of the B-Galactosidase marker was evaluated using two groups of eight normal mice. Two mice were injected subcutaneously on the back, two mice were injected intramuscularly and two mice were injected in the footpad with Lac-Z transduced cells. One animal was injected with fibroblasts transduced with neo-marker only, and the last mouse was injected with untransduced fibroblasts. After harvesting and washing, the different cell lineages were suspended in a concentration of $10^7$ cells in 0.2 ml of Hank's Phosphate Buffered Saline (PBS) and slowly injected using a 25 gauge needle at different sites. Animals were sacrificed at 10 and 15 days post treatment and injection sites were submitted to histochemical study. Pieces of tissue were fixed in 4% paraformaldehyde for one hour, washed in PBS three times and then kept in 8.4% acrylamide solution overnight. The next morning tissues were embedded in acrylamide which after hardening were cut and frozen. The frozen sections were done in 10 μm by cryostat and stained with 1 ml of 5-Bromo-4-chloro-3-indolyl-B-d-galactopyranoside (X-Gal) in PBS. The X-Gal was dissolved in DMSO at 40 mg/ml and then added to the reaction mixture. Incubation was for 14-18 h at 37° C. FIG. 6 illustrates B-Gal expression in transduced fibroblasts 60 days in vivo. There was no evidence of an inflammatory response, suggesting that the retrovirus used to transduce syngeneic fibroblasts, does not evoke an immune response or rejection process.

2. Effect of PLP in Normal SJL Mice

Another important aspect of this invention in the embodiment of this example is determining whether transduced fibroblasts secreting PLP actually produce EAE in normal animals. To test this, 107 PLP-secreting SJL fibroblasts were injected into 12 normal SJL mice. Six animals had fibroblasts placed subcutaneously and six animals had fibroblasts injected intraperitoneally. Animals were sacrificed at day 16 and showed no evidence of inflammatory disease or EAE. FIG. 7 illustrates the clinical scoring system for chronic EAE. [Lu, Y.-A., et al., Mol. Immunol., 28:623-630 (1991); Williamson, J., et al., J. Neuroimmunol., 32:199-207 (1991).] In the EAE model for multiple sclerosis, using spinal cord homogenates plus adjuvant, inflammation in the CNS can be seen by day 14. In this study, normal animals injected with PLP-secreting SJL fibroblasts did not show any signs of clinical disease even at day 60. In addition, the animals did not show any histologic evidence of inflammation in the CNS at day 60. FIG. 8 illustrates the histological scoring system for EAE. [Govemman, J., et al., Cell, 72:551-560 (1993).]

3. Clinical and Histological Assessment of Acute EAE Mice Treated with Retrovirus Transduced Fibroblasts.

Six week old SJL mice were injected with mouse spinal cord homogenate (MSCH) in complete Freund's Adjuvant (CFA) and with MSCH in incomplete Freund's Adjuvant IFA, seven days later. [Kennedy, M. K., et al., J. Immunol., 144: 909-915 (1990).] The initial EAE attack was observed on days 14-18, with full recovery by day 21. Ninety-five percent of animals showed clinical evidence of an acute attack. These animals were divided into five groups which were either left untreated or were given either $10^7$ PLP secreting SJL fibroblasts or control fibroblasts (untransduced cells, β-gal-producing cells, or "empty" vector-transduced cells) on day 21. Animals not showing clinical disease were eliminated from the experiment.

Figure 9A:
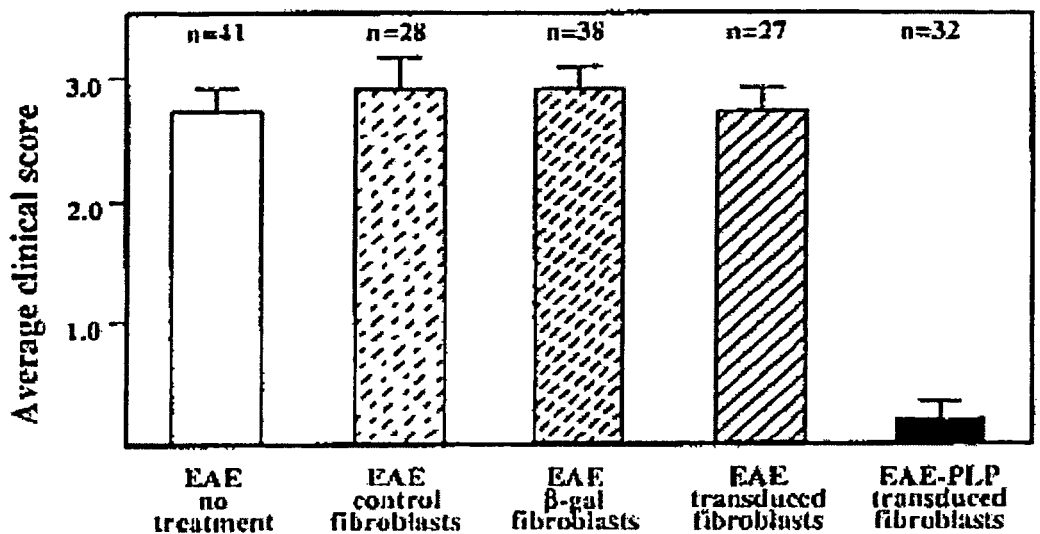
FIG. 9A illustrates the clinical score of EAE mice with a first relapse treated by injection of PLP-secreting fibroblasts. The treatment groups are shown on the abscissa and the average clinical score is shown on the ordinate.
Figure 9B:
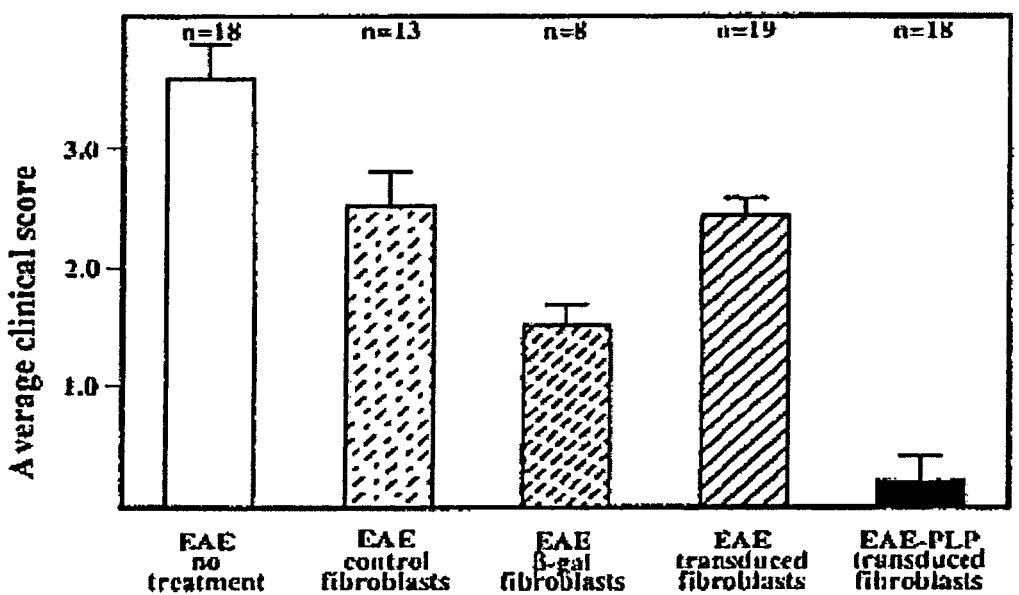
FIG. 9B illustrates the average clinical score of EAE mice with a second relapse treated by injection of PLP-secreting fibroblasts. The treatment groups are shown on the abscissa and the average clinical score is shown on the ordinate.
Figure 10A:
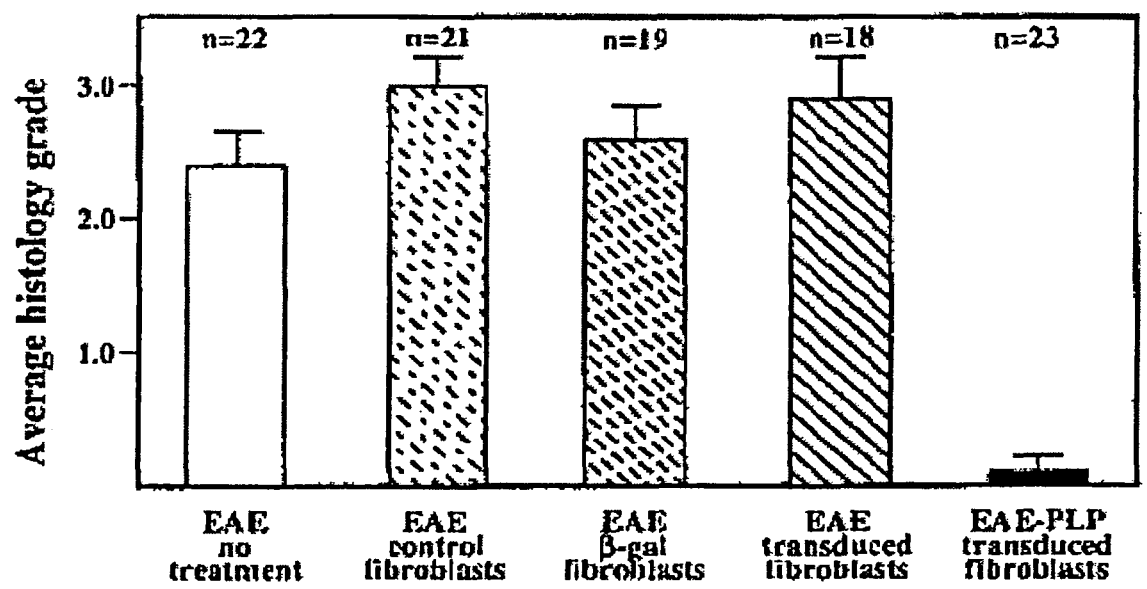
FIG. 10A illustrates the histology score of EAE mice with a first relapse treated by injection of PLP-secreting fibroblasts. The treatment groups are shown on the abscissa and the average histology score is shown on the ordinate.
Figure 10B:
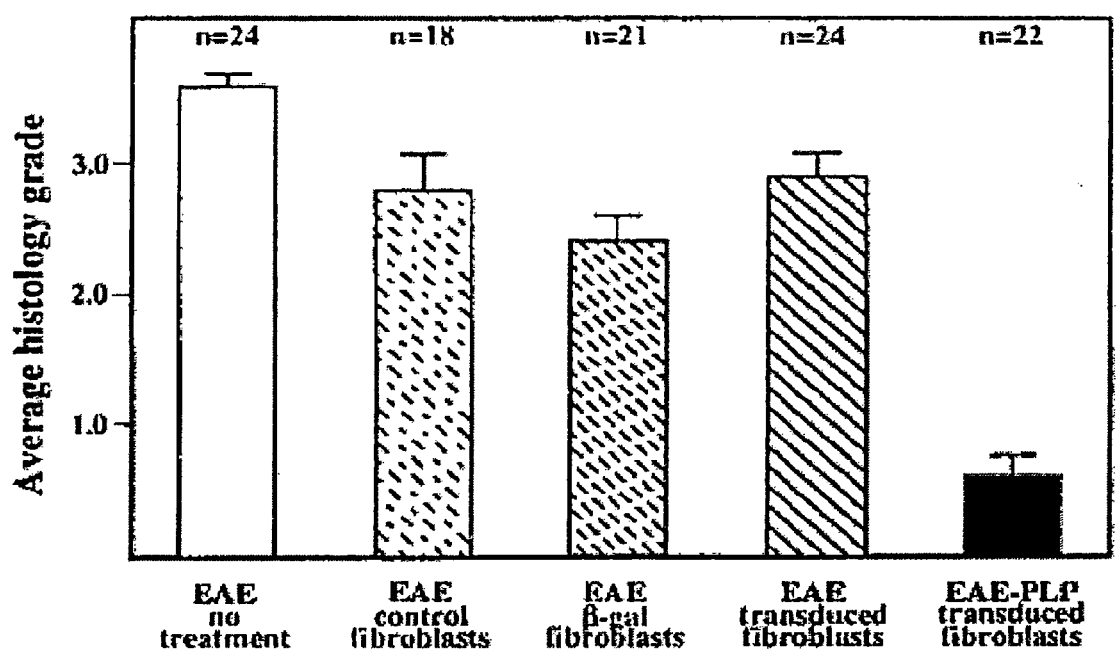
FIG. 10B illustrates the histology score of EAE mice with a second relapse treated by injection of PLP-secreting fibroblasts. The treatment groups are shown on the abscissa and the average histology score is shown on the ordinate.

FIGS. 9A and 9B illustrates the clinical assessment of EAE mice, in first and second relapse, respectively, treated with retrovirus transduced fibroblasts. Animals receiving the PLP secreting fibroblasts, column E, in both FIGS. 9A and 9B had a marked reduction of clinical signs and had dramatic reduction in inflammatory cells, particularly in the brain. FIG. 10A and 10B illustrates the histology grade of of EAE mice, in first and second relapse, respectively, treated with retrovirus transduced fibroblasts. Animals receiving the PLP secreting fibroblasts, column E, in both FIGS. 10A and 10B had a marked reduction of histological signs of EAE mice, in first and second relapse, respectively, treated with retrovirus transduced fibroblasts whereas untreated control animals typically showed cuffs of perivascular inflammation in the brain, spinal cord, and subarachnoid space, with focal infiltration of inflammatory cells into the parenchyma and fold demyelination.

4. Histological Assessment of Late Stage EAE Mice Treated with Retrovirus Transduced Fibroblasts.

Figure 11:
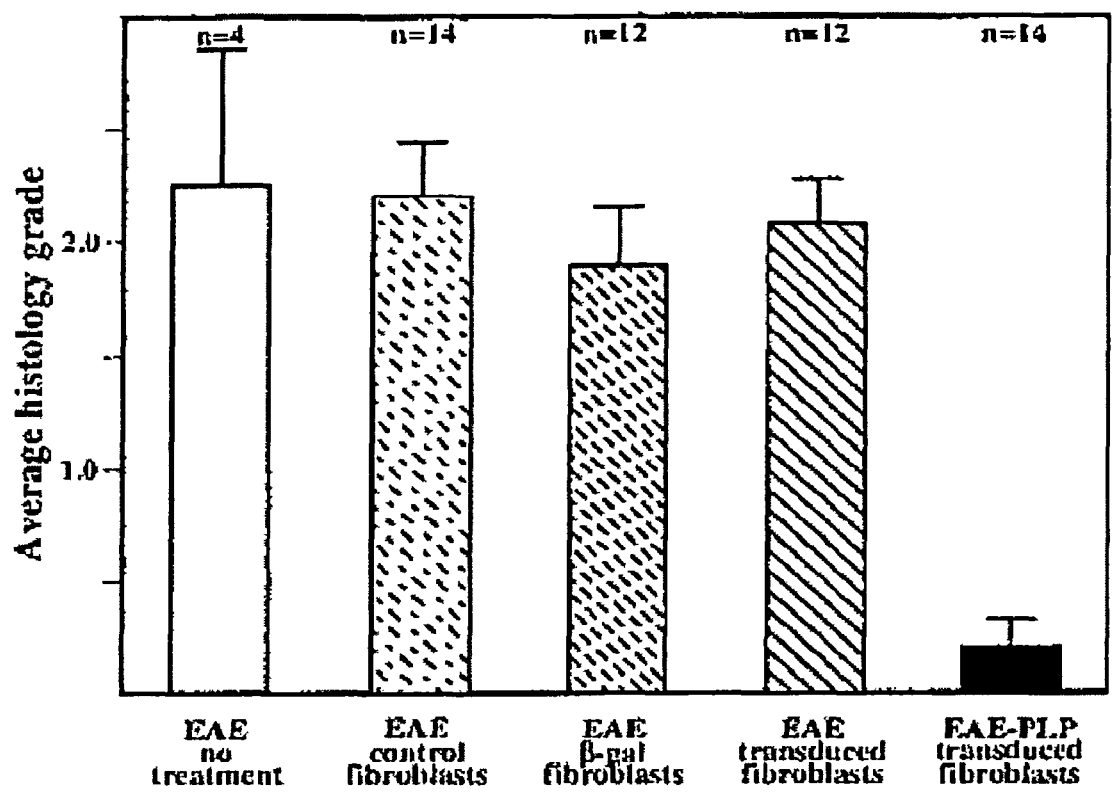
FIG. 11 illustrates the histology score of late-stage disease EAE mice treated by injection of PLP-secreting fibroblasts. The treatment groups are shown on the abscissa and the average histology score is shown on the ordinate.

The effect on EAE of having PLP-secreting fibrolasts injected late in the disease course after multiple relapses also was examined. PLP-secreting fibroblasts were injected into previously untreated EAE mice on day 145, 8 to 10 days after the third relapse. The animals were sacrificed 23 days later. Disease is assessed by histology grade. Histology scores, read blindly, of mice receiving the PLP-secreting fibroblasts were significantly reduced compared with those mice receiving either no treatment or control cells ($p<0.01$). FIG. 11 shows this data and that late-stage disease in mice with EAE is abrogated by injection of PLP-secreting fibroblasts. The injection of PLP-secreting fibroblasts reduces the frequency and severity of EAE relapses and ameliorates the pathological destruction.

5. Peripheral Immune Status of Treated Mice v. Control EAE Mice

Spleen cells from four EAE control mice and from four EAE mice which had been treated with fibroblasts expressing the PLP protein were used in proliferation assays, in which they were incubated with 40 μM PLP peptide 139-151 or 40 μM HIV gp120 peptide 308-322 for 4 days and then pulsed with $^3$H-thymidine for 24 hours.

Briefly, animals were sacrificed by $CO_2$ asphyxiation. Spleen cells were dispersed to single cell suspensions in RPMI 1640 by passing through a size 60 mesh, and washed once before being cultured ($8\times10^5$ per well) in 0.2 ml of HL-1 medium (Hycor Biomedical, Irvine, Calif.), supplemented with 2 mM glutamine, 100 U/ml penicillin, 100 μg streptomycin either alone or with 40 μM of peptide in 96-well tissue culture plates for 4 days at 37° C. with 5% $CO_2$. PLP peptide 140-151 were used for antigen-specific proliferation while HIV gp120 peptide 308-322 was used as negative control.

Where indicated, some wells also contained 10 U/ml of recombinant mouse IL-2 (Boehringer Mannheim, Indianapolis, Ind.). During the last 18-24 h of culture, each well was pulsed with 1 μCi of $^3$H-thymidine (ICN, Irvine, Calif.), harvested onto 'Xta1 Scint' glass fiber filters (Beckman, Fullerton, Calif.) and counted using a Beckman LS6000 Scintillation counter. Thymidine incorporation values (experimental counts per minute—background counts per minute) were calculated and represent means of triplicate cultures±standard deviation.

Figure 12:
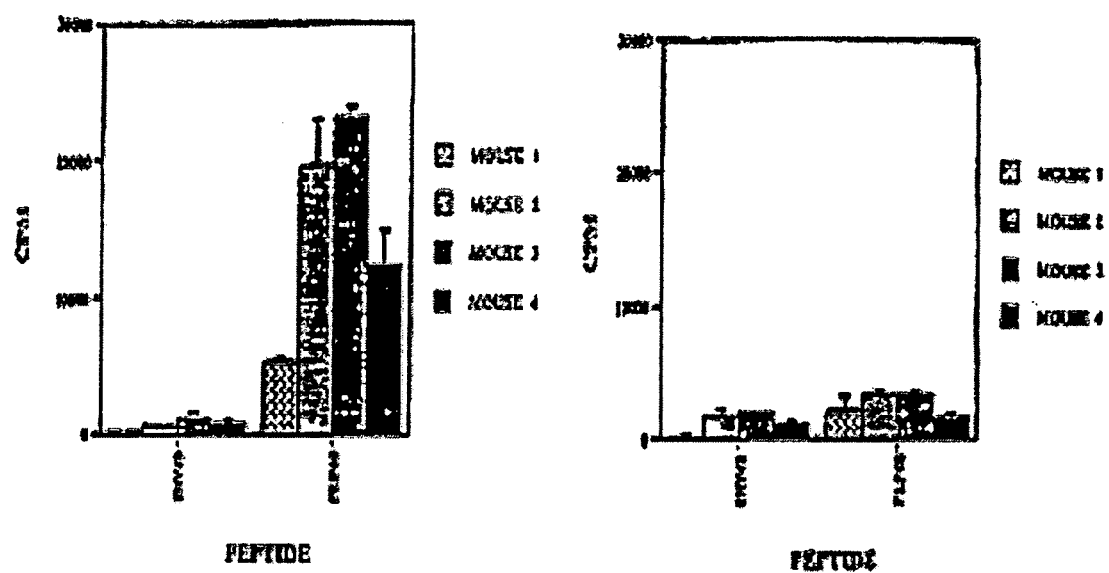
FIG. 12 illustrates the results of proliferation assays using EAE mice treated with PLP-expressing fibroblasts.

The results are shown in FIG. 12 and suggest that PLP specific proliferative responses are reduced significantly in EAE mice which have received PLP expressing fibroblasts.

Figure 13:
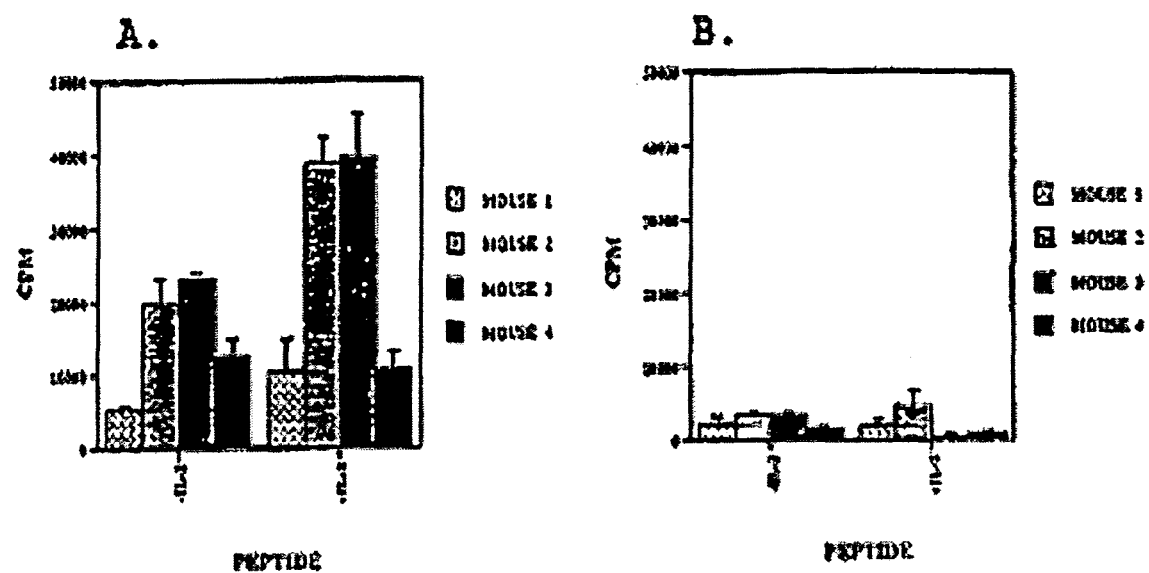
FIG. 13 illustrates the results of proliferation assays with and without IL-2 using EAE mice treated with PLP-expressing fibroblasts.

FIG. 13 illustrates the same experiment as in FIG. 12 but with the addition of mouse IL-2 (10 U/ml) for 5 days. These results illustrate that the mechanism by which the PLP specific proliferative responses are reduced significantly may suggest the silencing of T cells because these lymphocytes do not respond to IL-2.

The benefits of the treatment described above are clearly advantageous over alternative treatments. The method described herein is a genetic approach to immunospecifically silence pathogenic T-cell responses and does not down-regulate the entire immune system. In the case where an individual with a T-cell mediated autoimmune disease exhibits pathogenic T-cells of multiple specificities, the invention may easily be adapted to target those specificities. For example, DNA encoding multiple self-antigenic epitopes may be introduced into the patient's cells. The method is also advantageous in that the reagents can easily be made or obtained in sufficient quantity to carry out the method.

EXAMPLE 4

EAE is Abrogated in Mice Treated with MBP-Secreting Fibroblasts.

Figure 14:
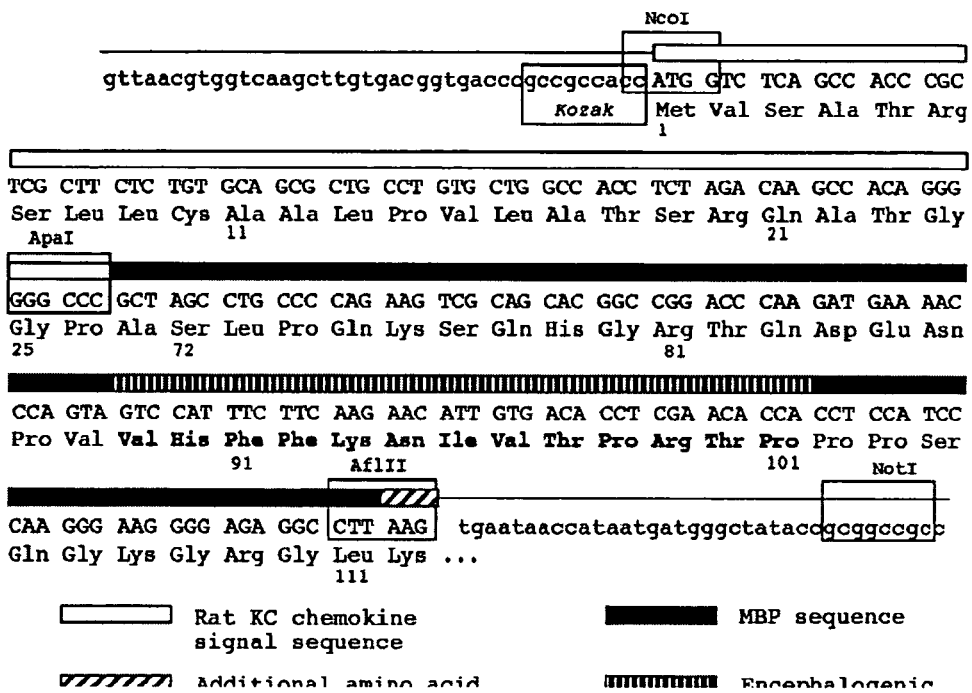
FIG. 14 is a map showing a construct having a nucleotide sequence corresponding to SEQ ID NO: 35 and encoding a polypeptide having an amino acid sequence corresponding to SEQ ID NO: 36. The construct encodes a partial MBP gene product, amino acids 71-111 (encoded by SEQ ID NO: 10), with a RAT KC chemokine leader sequence (encoded by SEQ ID NO: 9) and additional positively charged amino acid, lysine (encoded by SEQ ID NO: 12), for secretion.
Figures 15A, 15B:
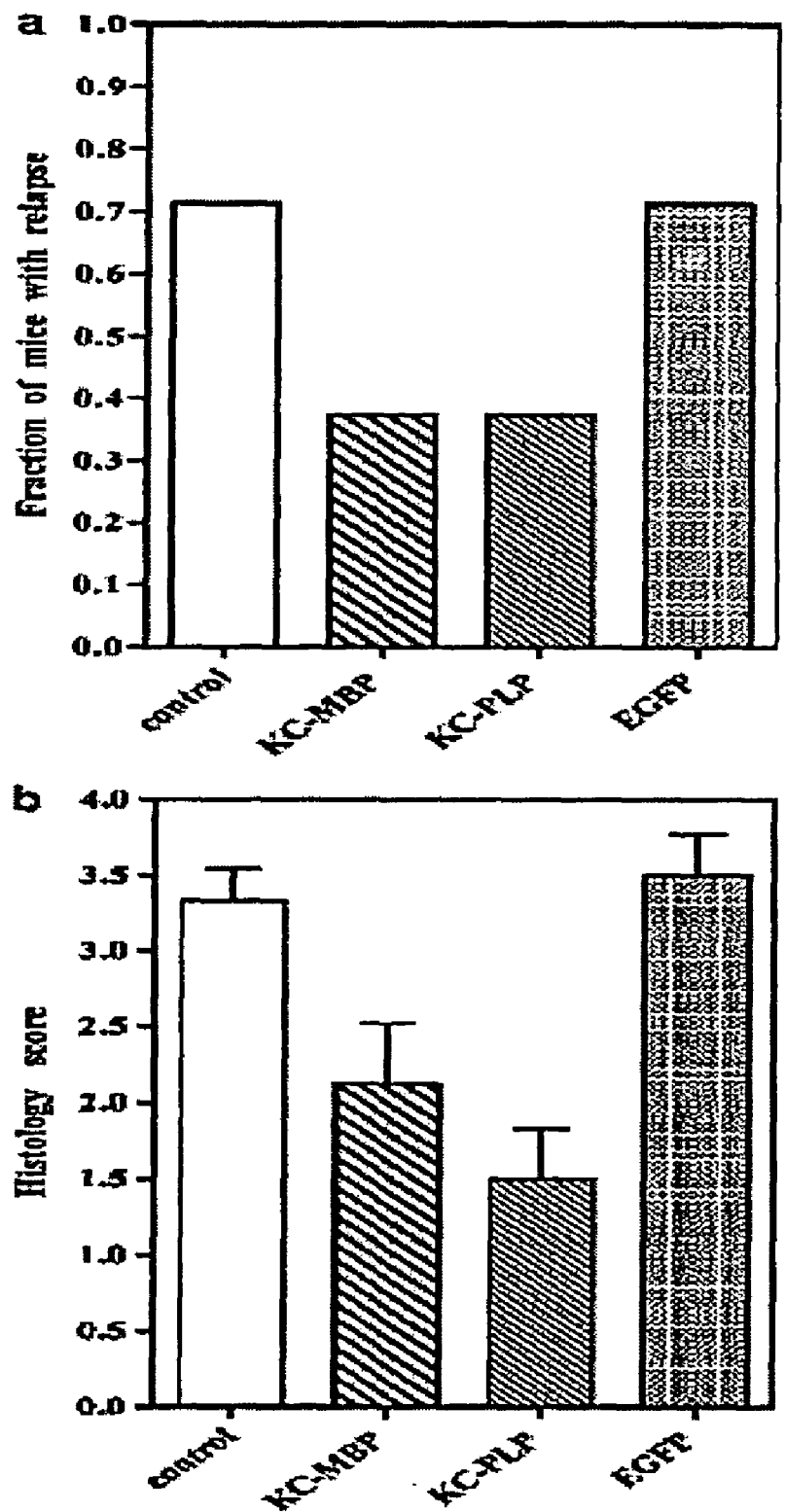
FIG. 15a is a graph showing the abrogation of EAE in mice by injection of MBP and PLP secreting fibroblasts as compared to controls (labeled control and EGFP) with the fraction of mice with relapse on the ordinate and the identity of the mice groups on the abscissa.
FIG. 15b is a graph showing the histology scores of the same mice of FIG. 15a with the histology score on the ordinate and the identity of the mice groups on the abscissa.

Treatment of mice suffering from EAE induced by MSCH with PLP-secreting fibroblasts can ameliorate disease. In order to determine whether this therapy has more general applicability and is not PLP-specific, transduced fibroblasts secreting an MBP epitope were used to treat MBP protein-induced EAE. A schematic diagram of the MBP construct (amino acids 71-111) is shown in FIG. 14 (SEQ ID NO: 15). The sources of the sequences are indicated in boxes beneath the text. RT-PCR analysis of the MBP-secreting fibroblasts was used to demonstrate the presence of MBP-specific RNA. Seven week-old female SJL/J mice were injected on day 0 with MBP protein in CFA and pertussis toxin, followed by 400 ng pertussis toxin on day 2, and MBP protein in CFA on day 7. The initial EAE attack was observed between days 10-14, with the first relapse occurring between days 35-45. Animals with clinical evidence of an acute attack were divided into the following four treatment groups (n=8): 1) untreated control, 2) MBP-secreting fibroblasts, 3) PLP-secreting fibroblasts, and 4) control enhanced green fluorescent protein (EGFP)-expressing fibroblasts. Control mice received no treatment. The remaining groups received 2×10$^6$ SJL cells transduced with either vectors KC-MBP-pBIB, KC-PLP-pBIB, or EGFP-pBIB, respectively. The fraction of mice relapsing is shown in FIG. 15a and the histology scores in FIG. 15b. The identity of the mouse groups (n=8 for all groups) is indicated on the abscissa. Animals receiving either MBP- or PLP-secreting fibroblasts exhibited a lower relapse rate (FIG. 15a) and when sacrificed, after the first relapse, had dramatic reductions in inflammatory cells in the brain and spinal cord ($p<0.05$ for MBP-treated animals, $p<0.005$ for PLP-treated animals) (FIG. 15b) compared to the two groups of control animals. In particular, mice receiving the PLP-secreting fibroblasts had strikingly reduced lymphocytic infiltration in the brain. Thus, both MBP- and PLP-secreting fibroblasts were capable of successfully treating MBP protein-induced disease.

Cell Lines.

An SJL/J fibroblast line, designated LBW 1B2 (L13W), was obtained from Dr. G. Dreskler (Uniformed Services University, Bethesda, Md.) and grown at 37° C., 5% $CO_2$ in RPMI medium (Mediatech, Herndon, VA) supplemented with 10% FCS (BioWhittaker, Walkersville, Md.), 50 U/ml penicillin, 50 mg/ml streptomycin, and 2 mM L-glutamine (all Irvine Scientific, Santa Ana, Calif.) (RPMI-10). An SJL/J primary cell line (SJL) was established from a dorsal skin explant as detailed in Freshney. [Freshney, R. I., Culture of Animal Cells, 2nd ed. Alan R. Liss, Inc.: New York, 1987.] The cell line was grown in RPMI supplemented with 20% FCS, 100 U/ml penicillin, 100 mg/ml streptomycin, 100 mg/ml gentamicin (Sigma, St Louis, Mo.) and 2 mM L-glutamine (RPMI-20). A NOD/LtJ primary cell line was derived from embryos as described and grown in RPMI-20. [Freshney RI. Culture of Animal Cells, 2nd ed. Alan R. Liss, Inc.: New York, 1987.]

FACS Analysis of Primary Cell Line.

The SJL/J primary cell line was analyzed for MHC class II expression using antibody 10-2.16 that recognizes the H2-As molecule. [Oi,V.T., et al., Curr Top Microbiol. Immunol., 81: 115-120 (1978).] SJL/J spleen cells were used as a positive control. Antibody 28-14-8 was used as an isotype control. [Ozato, K., et al., J. Immunol., 125: 2473-2477 (1980).]

Vectors.

Construction of the mini-gene encoding PLP 101-157 (SEQ ID NO.: 3) in both the expression plasmid PLP-pRc/CMV and in a retroviral vector (designated Ld-PLP) has been described above. The retroviral expression plasmid PLP-pBIB was generated by subcloning the NcoI-BamHI fragment from PLP-pRc/CMV into the NcoI-BamHI site of pBIB-KMS, an expression vector containing an upstream Kozak eukaryotic translation initiation site [Kozak M., Nucleic Acids Res. 12:857-872 (1984)] and the bsr gene which permits blastocidin-S selection of transductants. [Fling, S. P., et al., Proc. Natl. Acad. Sci. U.S.A., 98: 1160-1165 (2001).] To construct the KC-PLP-pBIB vector, two complementary pairs of oligonucleotides coding for the 72 base pair long rat KC chemokine leader sequence [Huang, S., et al., Biochem. Biophys. Res. Commun., 184: 922-929 (1992)] were first synthesized and 400 pmoles of each complementary oligonucleotide were annealed in 0.02M Tris pH 7.2, 0.1M NaCl using a Perkin-Elmer 9600 thermocycler programmed to cool from 100° C. to 60° C. in 90 minutes. The two annealing reactions were then combined and returned to the thermocycler and cooled from 60° C. to 25° C. in 90 minutes. The annealed KC leader was digested with BstEII and ApaI and subcloned into PLP-pRc/CMV using the same restriction sites to create the vector KC-PLP-pRc/CMV. The retroviral vector KC-PLP-pBIB was then constructed by subcloning the NcoI-BamHI fragment of KC-PLP-pRc/CMV into pBIB-KMS. See FIG. 21.

The mini-gene encoding MBP (71-111) (SEQ ID NO: 15) (FIG. 14) was generated using synthetic oligonucleotides. Complementary pairs of oligonucleotides were annealed and ligated using standard procedures. The correct MBP product was isolated from the ligation reaction by electroelution from a 7 M urea/8% acrylamide gel. To create the MBP-pRc/CMV vector, the PLP-pRc/CMV plasmid was digested with ApaI and AflII then run on a 2% agarose gel to remove the PLP mini-gene. The ApaI/AflII-digested vector was eluted from the gel using GeneClean (Bio10, La Jolla, Calif.) and then ligated to the MBP DNA. The KC leader sequence was cloned into MBP-pRc/CMV as detailed above for the PLP-pRc/CMV construct, generating the vector KC-MBP-pRc/CMV. In order to clone the KC-MBP sequence into pBIB-KMS, a NotI site was introduced into the KC-MBP-pRc/CMV vector downstream of the MBP sequence using a QuikChange Site-Directed Mutagenesis Kit (Stratagene, La Jolla, Calif.) (see FIG. 14). The KC-MBP sequence was then sub-cloned into pBIB-KMS using NcoI and NotI to create the vector KC-MBP-pBIB.

Transduction of Fibroblast Cells.

Amphotropic retroviral particles carrying the PLP-pBIB, KC-PLP-pBIB, KC-MBP-pBIB, or enhanced green fluorescent protein (EGFP)-pBIB constructs were produced by transient transfection of the high-titer retroviral helper packaging line, Phoenix-Ampho. [Pear, W. S., Scott, M. L., Nolan, G. P. In: Robbins P (ed). Methods in Molecular Medicine: Gene Therapy Protocols. Humana Press: Totowa, N.J., 1996, pp. 41-57.] For transfections, 0.15 mg of plasmid DNA for each construct was precipitated by the addition of 0.25M $CaCl_2$ and Hank's balanced salt solution in a final volume of 150 ml. The precipitated DNA was added drop-wise to wells of a 6-well plate containing 1.5 ml/well Phoenix-Ampho cells that had been seeded 18 hours earlier in DMEM (Mediatech) supplemented with 10% FCS (DMEM-10) at a density of $0.5 \times 10^6$ cells/ml. After 6 hours at 37° C., medium was replaced with fresh DMEM-10. After 24 hours, transfected Phoenix-Ampho cells were placed at 32° C. for 18 hours, after which supernatants containing retrovirus were collected, centrifuged to remove cells and stored at −80° C. For transduction of the fibroblast cells, a series of two-fold dilutions of target cells starting with $1 \times 10^4$ cells/well in 0.5 ml were plated in a 24-well plate one day prior to transduction. On the day of transduction, wells which were ⅓ to ½ confluent received undiluted viral supernatant (0.5 ml) and 10 mg/ml DEAE/Dextran (Sigma); control wells received 0.5 ml medium supplemented with DEAE/Dextran. Plates were centrifuged at 1800 rpm for 30 min at 4° C. then incubated overnight at 32° C. in 5% $CO_2$. The viral supernatant was then aspirated and replaced with RPMI-10 and the cells were transferred to a 37° C., 5% $CO_2$ incubator. Upon reaching confluency, cells were expanded and grown in selection medium (RPMI-10 supplemented with 10 mg/ml blasticidin S (Calbiochem, La Jolla, Calif.)).

Analysis of PLP-Specific and MBP-Specific mRNA Expression.

RNA was isolated from $4 \times 10^6$ cells using RNAzol B (Tel-Test, Inc., Friendswood, Tex.). The final RNA product was resuspended in diethylpyrocarbonate (DEPC)-treated double-distilled (dd)H2O. RT-PCR analysis was performed on 1 mg of RNA using the GeneAmp RNA PCR Kit (Perkin-Elmer/ABI). The following primers were used for PLP: 5' GCGACTACAAGACCACCATCT-3' (SEQ ID NO: 27) and 5' TAAGGCTAGCATAGGTGATG-3' (SEQ ID NO: 28). The MBP-specific primers were 5' GCTAGCCTGCCCCA-GAAGTCG-3' (SEQ ID NO: 29) and 5° CTTAAGGC-CTCTCCCCTTCCCTTG-3' (SEQ ID NO: 30). The RT-PCR product was analyzed on a 1.5% agarose gel and DNA of the correct size was isolated and submitted for automated sequencing.

Induction of EAE in SJL/J Mice.

Six week-old female SJL/J mice (Jackson Laboratory, Bar Harbor, Me.) were each injected with an identification chip (AVID Technology, Norco, Calif.). To induce EAE using mouse spinal cord homogenate (MSCH), seven week-old mice were injected subcutanteously (s.c.) on the lower back with 0.7 mg MSCH in CFA on day 0 and boosted on day 7 with the same dose of MSCH in IFA. Typically, the initial EAE attack was observed between days 14-18, with full recovery by day 21. The first relapse usually occurred between days 45-55.

To induce disease with MBP protein, seven week-old mice were injected s.c. on the lower back with 0.8 mg bovine MBP protein (Sigma) in CFA and 400 ng pertussis toxin (Sigma) injected intraperitoneally (i.p.) on day 0, followed by 400 ng pertussis toxin i.p. on day 2, and 0.8 mg MBP protein in CFA on day 7. The initial EAE attack was usually observed between days 10-14, with the first relapse occurring between days 35-45.

Treatment of EAE Mice with Retrovirally Transduced Fibroblasts.

Only animals developing clinical disease were used for further study. By day 21 all mice had recovered from their initial attack. Animals were then divided into groups prior to initiation of treatment on day 23 (number of mice per group is indicated in each figure legend). One group of mice comprised the untreated control. Mice receiving treatment with fibroblasts were injected s.c. in the neck/shoulder area. Mice were checked daily and the level of disease was evaluated according to the following scale: 0=normal; 1=slow, sluggish; 2=limp tail; 3=limp tail, hind limb weakness, waddling gait; 4=partial hind limb paralysis; 5=complete hind limb paralysis; 6=immobile; 7=moribund. Between days 65-70, animals were sacrificed and their brain and spinal cord removed and coded for blinded histological examination. See FIG. 7.

Statistical Analyses.

Histological data were analyzed for statistical significance using an unpaired t test (Graph Pad Prism, Graph Pad Software, Inc., San Diego, Calif.).

EXAMPLE 5

Change in the Leader Sequence Reduces the Effective Dose of Transduced Cells.

Figure 16A:
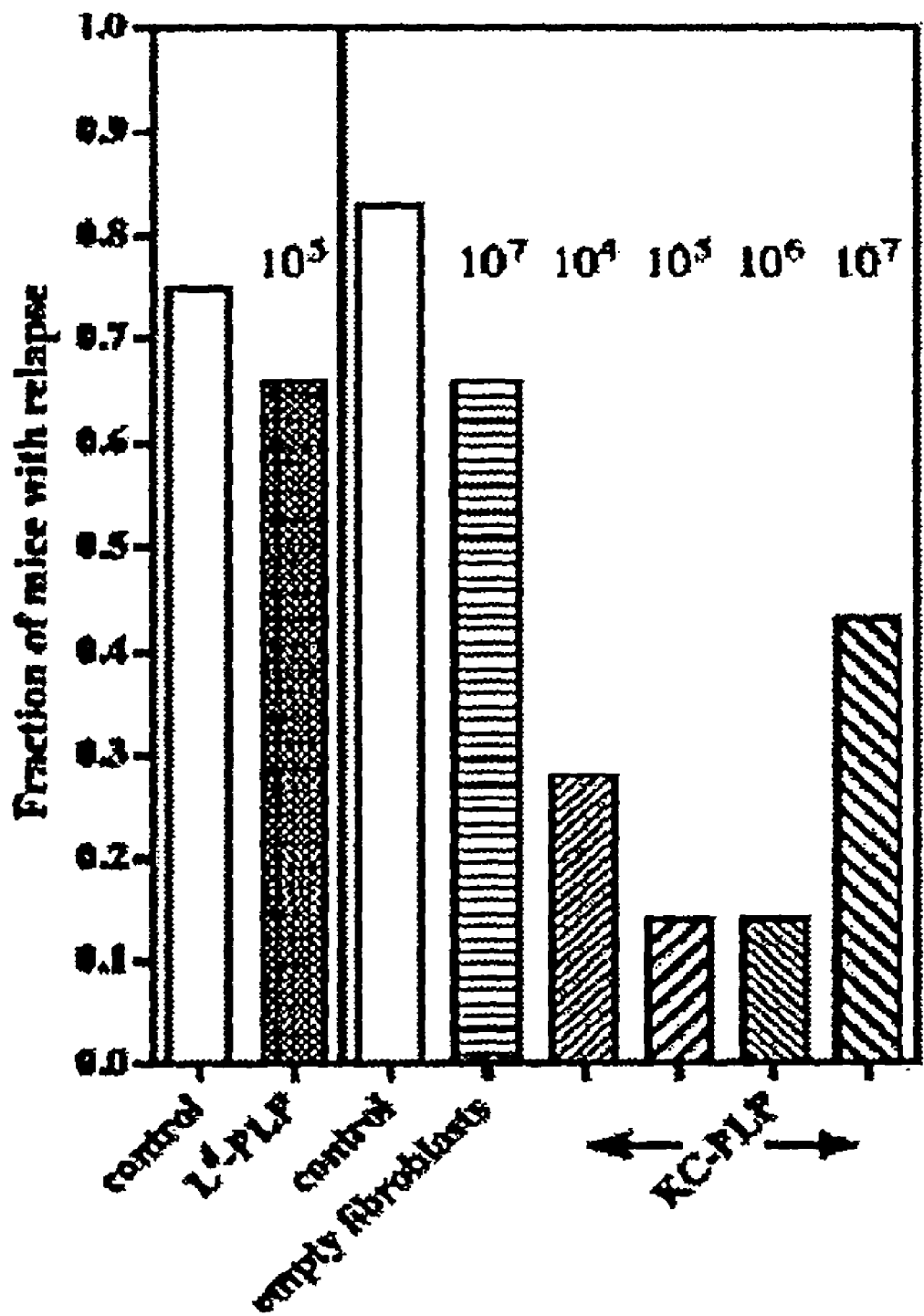
FIG. 16a is a two paneled graph with the fraction of mice with relapse on the ordinate and identity of the mice groups on the abscissa showing the efficacy of PLP-secreting fibroblasts depending on the leader sequence and on the number of cells injected.
Figure 16B:
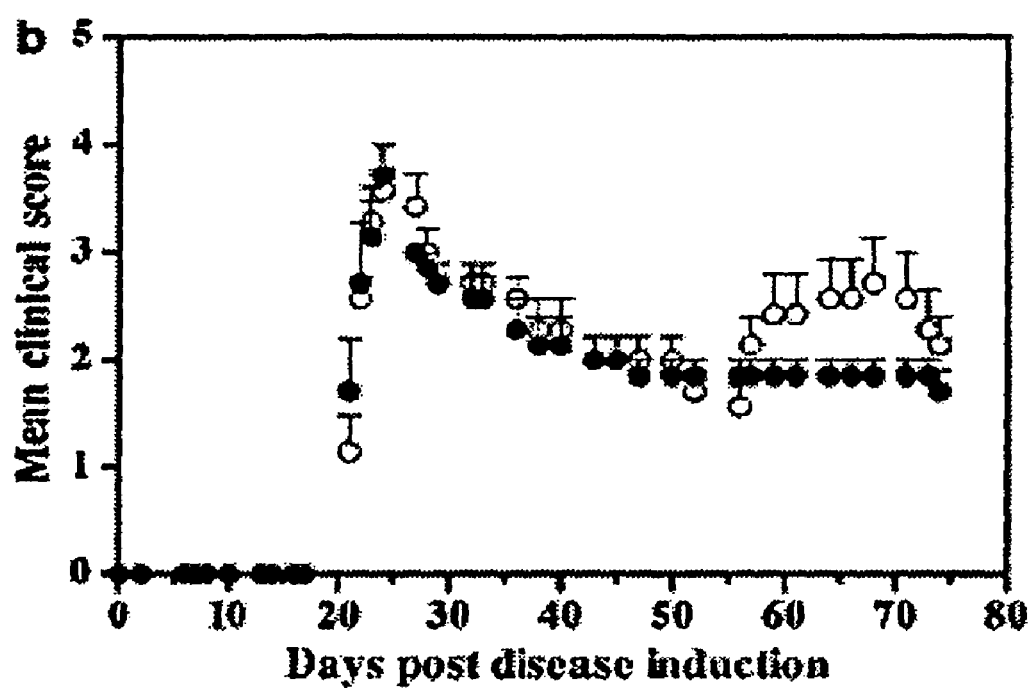
FIG. 16b is a graph with mean clinical score on the ordinate and days post disease indication on the abscissa comparing the mice treated with $1 \times 10^5$ KC-PLP transduced fibroblasts (black dots) and untreated mice (white dots).

An important aspect in designing an antigen-specific therapy involves efficient production of the antigen. The leader sequence targets a globular protein to the endoplasmic reticulum for eventual constitutive secretion. [Gierasch, L. M., Biochemistry, 28: 923-930 (1989).] A signal sequence derived from a protein which is secreted, such as a chemokine, (see FIG. 14 and 21) could be more efficient at producing product than a leader sequence from a transmembrane protein, H2-$L^d$ (see FIG. 1), which is described above in the PLP mini-gene construct ($L^d$-PLP). Therefore, this signal sequence was replaced with that from the secreted protein rat KC chemokine. [Huang, S., et al., Biochem. Biophys. Res. Commun., 184: 922-929 (1992).] In order to determine a dose response for the KC-PLP-secreting fibroblasts, a titration of injected cells was performed. These results were compared to those obtained when $1 \times 10^5$ fibroblasts transduced with the $L^d$-PLP vector were used to treat EAE mice. All mice had disease induced by injection of MSCH. FIG. 16a shows the identity of the mouse groups indicated on the abscissa and the fraction of mice suffering a relapse is shown on the ordinate. The number of fibroblasts injected per mouse is also shown in each histogram. In the left-hand panel, control mice (n=8) received no treatment and EAE mice (n=8) received an injection of $1 \times 10^5$ $L^d$-PLP transduced fibroblasts. In the right-hand panel control mice (n=7) received no treatment, "empty" fibroblast mice (n=6) received an injection of untransduced fibroblasts, KC-PLP mice (n=7) received varying numbers of fibroblasts transduced with the KC-PLP-pBIB construct. FIG. 16a demonstrates that injection of either $1\times10^6$ or $1\times10^5$ KC-PLP-transduced cells into EAE mice ameliorates disease in marked contrast to $1\times10^5$ $L^d$-PLP transduced fibroblasts which were ineffective. Thus, mice are routinely treated by injecting $5\times10^5$ KC-PLP cells in contrast to the dose of $1\times10^7$ $L^d$-PLP cells. FIG. 16b shows the time-course of the mean clinical scores of the mice (n=7) that either received no fibroblasts (○)or have been treated with $1\times10^5$ KC-PLP fibroblasts(●), from the induction of disease to their sacrifice p<0.08 at day 68. The results clearly show that the effect of even $1\times10^5$ PLP-secreting fibroblasts is significant, again confirming the efficacy of the therapy.

EXAMPLE 6

Therapy is not Cell Line-Dependent.

Figure 17:
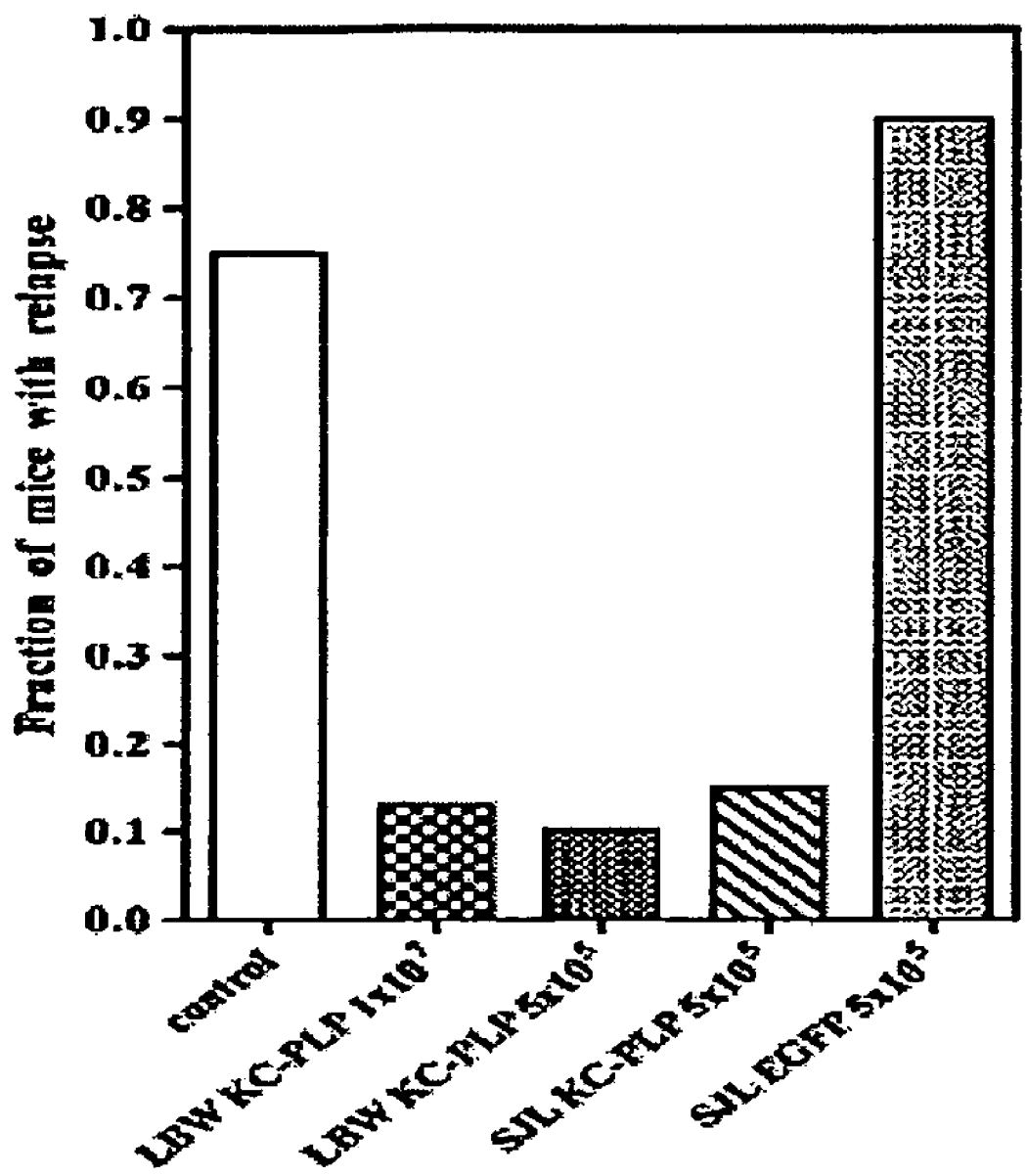
FIG. 17 is a graph showing the efficiency of transduced syngeneic fibroblasts does not depend on the identity of the cell line transduced with the fraction of mice with relapse on the ordinate and the identity of the mice groups on the abscissa.

The LBW cell line used in these studies is an untransformed fibroblast line. In order to ensure that successful treatment of EAE animals was not cell line-dependent, a primary line from explanted SJL/J skin was established. These cells (SJL) were then transduced with KC-PLP-pBIB, selected on blastocidin-S and tested for their ability to treat EAE. Disease was induced in all mice by injection of MSCH. FIG. 17 shows control mice (n=8) that received no treatment. The remaining groups received LBW cells transduced with the KC-PLP-pBIB vector, either $1\times10^7$ cells (n=10) or $5\times10^5$ cells (n=10), $5\times10^5$ SJL cells transduced with the same vector (n=12), or $5\times10^5$ SJL cells transduced with the EGFP gene (n=10). The identity of the mouse groups is indicated on the abscissa and the fraction of mice suffering relapses is shown on the ordinate. SJL cells transduced with KC-PLP-pBIB are as effective as transduced LBW cells; both PLP-secreting cell lines dramatically reduce the number of mice suffering relapses compared to mice treated with control SJL cells transduced with EFGP-pBIB. In conclusion, the effectiveness of the therapy is independent of the fibroblast line used.

EXAMPLE 7

Sequestered Cells Ameliorate EAE.

Figure 18:
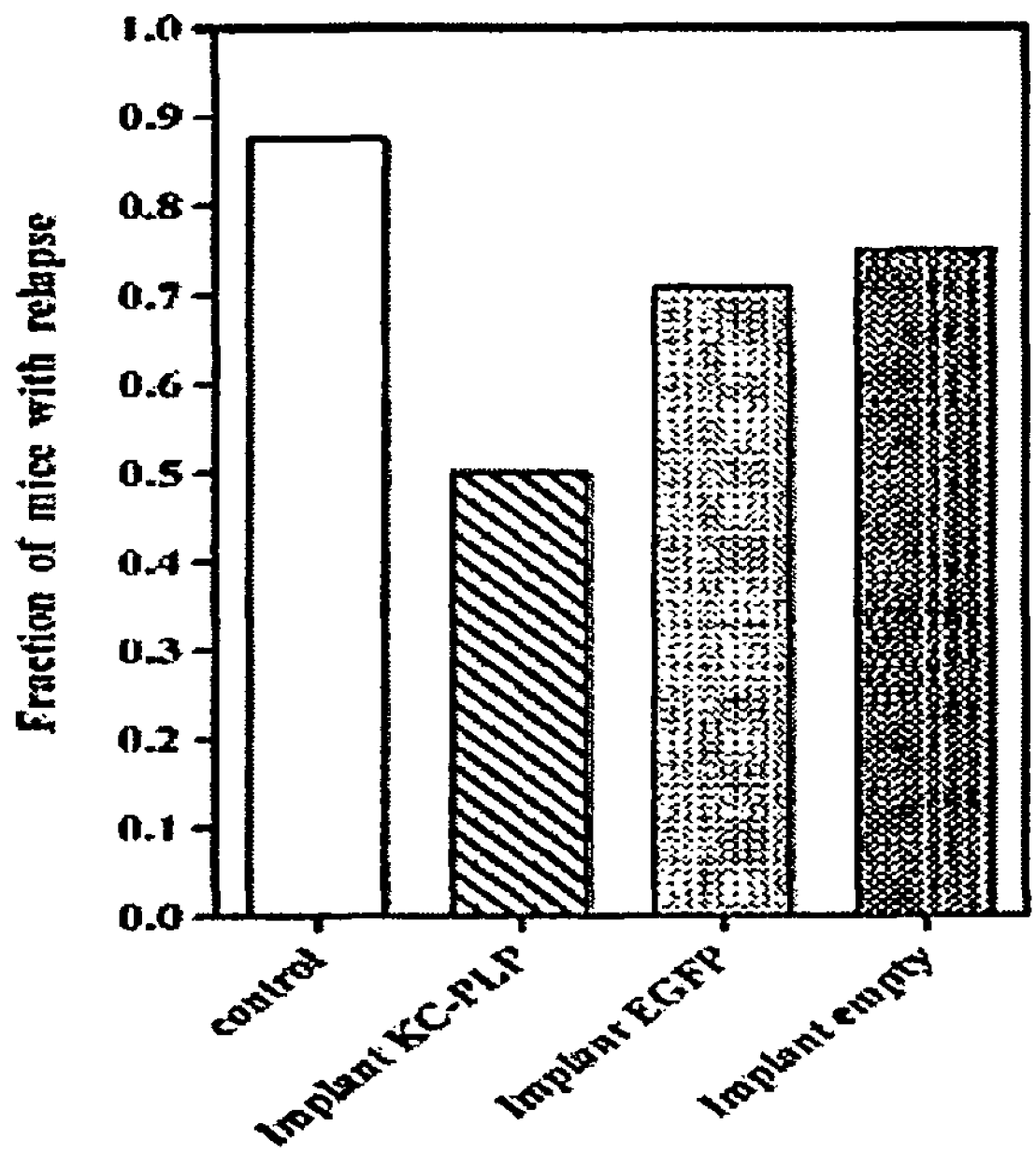
FIG. 18 is a graph showing that PLP-secreting fibroblasts sequestered within an implant reduced the relapse rate of EAE with the fraction of mice with relapse on the ordinate and the identity of the mice groups on the abscissa.
Figures 19A, 19B:
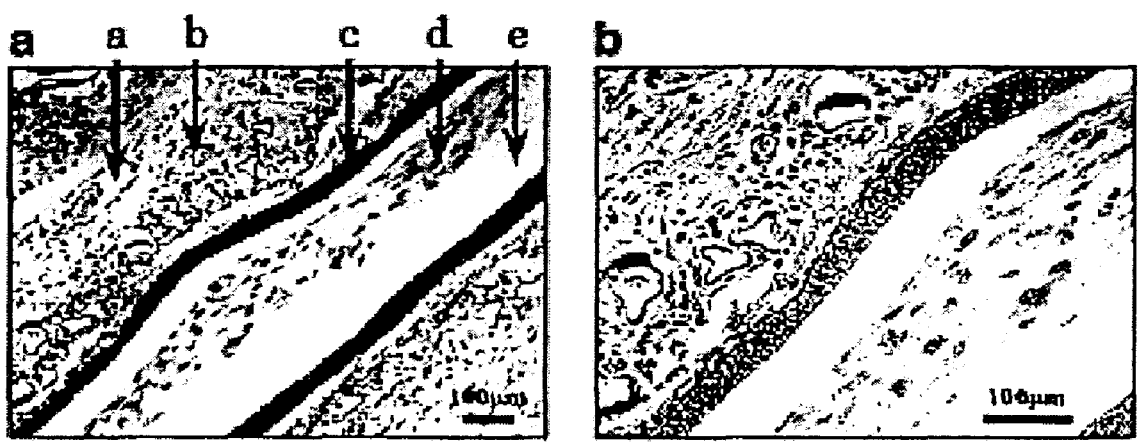
FIGS. 19a and 19b are photomicrographs showing PLP-secreting fibroblasts that survived for at least 42 days within a chamber.

For clinical use, a method for discontinuing this therapy, should any exacerbation occur, must be available. To address this issue, the transduced cells were placed within a sealed chamber that was implanted subcutaneously and which could be rapidly removed by surgery. This chamber is gas and liquid permeable, allowing the transduced cells to remain viable and peptides to be secreted into the surrounding tissue. [Tibell, A., et al., Cell Transplant, 10: 591-599 (2001); Yanay, O., et al., Hum. Gene Ther. 14: 1587-1593 (2003).] All mice had disease induced by injection of MSCH. Transduced fibroblasts were loaded into the chambers and implanted subcutaneously on the backs of SJL/J mice. The mice received either empty implants (control mice) or implants containing PLP- or EGFP-producing cells ($5\times10^5$ SJL cells transduced with either KC-PLP-pBIB or EGFP-pBIB) on day 24 after disease induction. FIG. 18 shows the identity of the mouse groups (n=8 for all groups) on the abscissa. The fraction of mice suffering a relapse is shown on the ordinate. The data shown in FIG. 18 demonstrate that mice implanted with the SJL KC-PLP cells were less likely to relapse than mice implanted with SJL EGFP cells. The chamber alone had no effect on the disease. The animal was sacrificed on day 65 (post-induction) and the chamber was removed, fixed in formalin, sectioned, and stained with hematoxylin and eosin. Photomicrographs of chamber sections at the time of sacrifice (42 days post implantation) showed the presence of viable transduced cells within the chamber (FIG. 19a/b). Arrows in FIG. 19a indicate the following structures: a) blood vessel, b) non-woven polyester mesh fibers, c) cell impermeable membrane, d) transduced cells, e) histology artifact. FIG. 19b is a partial field of FIG. 19a at a higher magnification. Black bars represent 100 microns. Although some evidence of a mild foreign body tissue reaction was observed, this is a local reaction to the chamber and not immune rejection, since no tissue or perivascular, lymphocytic infiltrate was observed. Using the EGFP cells, cells continue to live and express the transgene up to 77 days post implantation.

Treatment of EAE Mice with Transduced Cells Sequestered within a Chamber.

TheraCyte 4.5 ml immunoisolation devices (TheraCyte, Irvine, Calif.) were loaded with transduced fibroblasts ($5\times10^5$ or $2\times10^6$ cells, depending on the experiment) and sealed according to the manufacturer's protocols. On day 23 post disease induction, mice were anesthetized with Averting (Aldrich, Milwaukee, Wis.) (0.017 ml/gm mouse weight) administered i.p., and the chamber was implanted subcutaneously on the back. Mice were checked daily for the level of disease as detailed above. Between days 65-70 the animals were sacrificed and their brain and spinal cord removed and coded for blinded histological examination. One animal which received an implant containing EGFP-secreting fibroblasts was kept alive until day 77 at which time the implant was removed and examined for the presence of viable cells by fluorescent microscopy.

Histology.

Coded sections from brain and spinal cord were read in blinded fashion and scored according to the following scale: 1+mild (1-3 small foci of inflammation); 2+moderate (more than 3-7 foci containing at least 10 mononuclear cells); 3+severe (large foci of 15-25 cells with perivascular and meningeal collections); 4+severe with necrosis (demyelination plus mononuclear cells in 3+state).

Post sacrifice, the immunoisolation devices were removed and fixed in 10% formalin, then sectioned and stained using hematoxylin and eosin by DDF Services (Carpentersville, Ill.). See FIG. 8.

EXAMPLE 8

Sequestered Allogeneic Cells are Efficacious in the Treatment of EAE.

Figure 20:
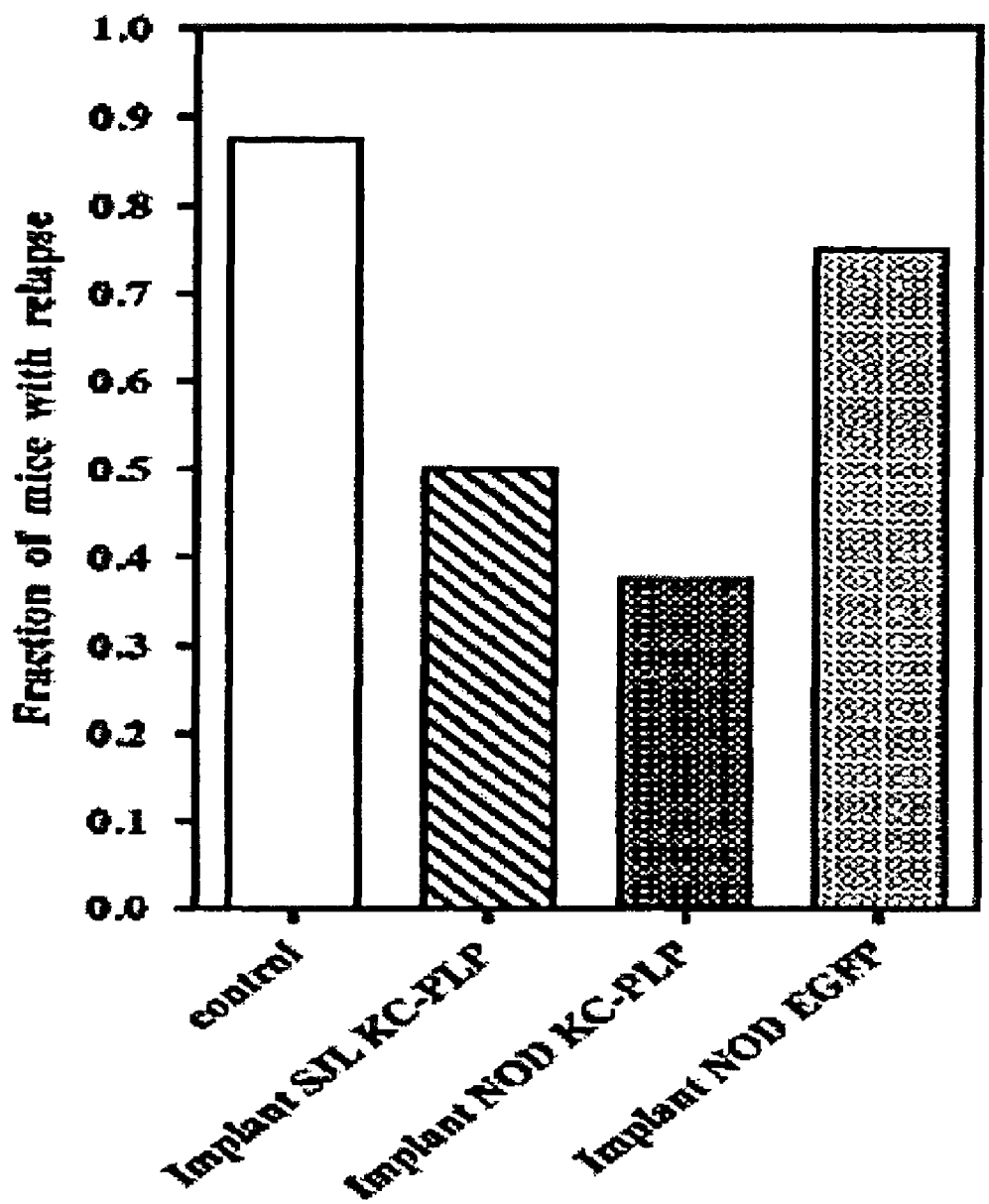
FIG. 20 is a graph showing allogeneic PLP-secreting NOD cells contained within an implant reduced the relapse rate in EAE mice with fraction of mice with relapse on the ordinate and the identity of the mice groups on the abscissa.

A major advantage of using cells confined within a chamber is the potential ability to use allogeneic cells, thus permitting one therapeutic cell line to be used for all patients. To assess the ability of a PLP-secreting allogeneic cell line to treat EAE in SJL/J mice ($H-2^s$) a primary NOD fibroblast cell line ($H-2^{g7}$) was transduced with either the pBIB-KC-PLP or pBIB-EGFP vectors. All mice had disease induced by injection of MSCH. FIG. 20 shows control mice that received no treatment and other mice that each received an implant filled with either $2\times10^6$ SJL cells transduced with KC-PLP-pBIB or $2\times10^6$ NOD cells transduced with the same or with the EGFP-pBIB vector. The identity of the mouse groups (n=8 for all groups) is indicated on the abscissa. The fraction of mice suffering a relapse is shown on the ordinate. PLP-secreting NOD cells were found to be equally effective at treating disease as are the PLP-secreting SJL cells. NOD cells transduced with pBIB-EGFP had no effect on disease. Thus, by containing the transduced cells within an implant, allogeneic cells can be successfully used.

The present invention is not to be limited in scope by the exemplified embodiments disclosed herein which are intended as illustrations of single aspects of the invention, and clones, DNA or amino acid sequences which are functionally equivalent are within the scope of the invention. Various modifications of the invention, in addition to those shown and described herein, will become apparent to those skilled in the art from the foregoing description. Such modifications are intended to fall within the scope of the appended claims.

All references cited herein are incorporated by reference.

What is claimed is:

1. A composition comprising:

a cell transduced with a polynucleotide encoding an antigenic amino acid sequence, wherein the cell expresses a therapeutically effective amount of the antigenic amino acid able to silence pathogenic T-cells to the expressed antigenic amino acid sequence in a patient, wherein the antigenic amino acid sequence is a portion of a complex antigenic molecule and is encoded by the nucleic acid sequence of SEQ ID NO: 10.

2. A kit comprising:

a cell transduced with a polynucleotide encoding an antigenic amino acid sequence, wherein the cell expresses a therapeutically effective amount of the antigenic amino acid to silence pathogenic T-cells to the antigenic amino acid sequence, wherein the antigenic amino acid sequence is a portion of a complex antigenic molecule and is encoded by the nucleic acid sequence of SEQ ID NO: 10;

a container therefore; and instructions for use.

3. The composition of claim 1, wherein the patient is a mammal.

4. The composition of claim 1, wherein the patient is a human.

5. The composition of claim 1, wherein the cell is allogeneic to the patient.

6. The composition of claim 5, wherein the cell is sequestered in a chamber.

7. The composition of claim 5, wherein the chamber is implanted into the patient subcutaneously.

8. The composition of claim 1, wherein the cell is a fibroblast.

9. The composition of claim 8, wherein the fibroblast is allogeneic to the patient.

10. The composition of claim 8, wherein the fibroblast is sequestered in a chamber.

11. The composition of claim 10, wherein the chamber is implanted into the patient subcutaneously.

12. The composition of claim 1, wherein the antigenic amino acid sequence comprises an encephalogenic amino acid epitope.

13. The kit of claim 2, further comprising a chamber.

14. The kit of claim 2, wherein the cell is an allogeneic cell to a patient.

15. The kit of claim 2, wherein the cell is a fibroblast.

16. The kit of claim 2, wherein the antigenic amino acid sequence comprises an encephalogenic amino acid epitope.

17. The kit of claim 2, wherein the antigenic amino acid sequence further comprises a leader sequence.

18. The kit of claim 17, wherein the leader sequence is derived from a secreted protein.

19. The kit of claim 18, wherein the secreted protein is a chemokine.

20. The kit of claim 2, wherein the antigenic amino acid sequence has a carboxyl terminus and further comprises at least one amino acid located at the carboxyl terminus with a positive charge.

* * * * *

UNITED STATES PATENT AND TRADEMARK OFFICE
CERTIFICATE OF CORRECTION

PATENT NO. : 8,323,963 B2  
APPLICATION NO. : 11/488524  
DATED : December 4, 2012  
INVENTOR(S) : Leslie P. Weiner et al.

Page 1 of 1

It is certified that error appears in the above-identified patent and that said Letters Patent is hereby corrected as shown below:

In the Claims:

Column 50, Claim 7, line 64, should read:

- The composition of claim 6, wherein the chamber is -

Signed and Sealed this
Fifth Day of March, 2013

Teresa Stanek Rea
*Acting Director of the United States Patent and Trademark Office*

SEQUENCE LISTING

```
<160> NUMBER OF SEQ ID NOS: 38

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1
gatggtgacc ggagatctgc cgccacc                                           27

<210> SEQ ID NO 2
<211> LENGTH: 78
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 2 atggggcga tggctccgcg cacgctgctc ctgctgctgg cggccgccct ggccccgact        60
cagacccgcg cggggccc                                                    78

<210> SEQ ID NO 3
<211> LENGTH: 57
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 3

Gly Asp Tyr Lys Thr Thr Ile Cys Gly Lys Gly Leu Ser Ala Thr Val
  1               5                  10                  15

Thr Gly Gly Gln Lys Gly Arg Gly Ser Arg Gly Gln His Gln Ala His
             20                  25                  30

Ser Leu Glu Arg Val Cys His Cys Leu Gly Lys Trp Leu Gly His Pro
         35                  40                  45

Asp Lys Phe Val Gly Ile Thr Tyr Ala
     50                  55

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

His Cys Leu Gly Lys Trp Leu Gly His Pro Asp Lys Phe
  1               5                  10

<210> SEQ ID NO 5
<211> LENGTH: 3
<212> TYPE: PRT
```

<213> ORGANISM: Artificial Sequence
<220> FEATURE:
<223> OTHER INFORMATION: Description of Artificial Sequence: Synthetic
      construct

<400> SEQUENCE: 5

Ser Leu Lys
 1

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 6
taggatcctt gaataggtaa gcttgctagc cc                                    32

<210> SEQ ID NO 7
<211> LENGTH: 5865
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7
tttgaaagac cccacccgta ggtggcaagc tagcttaagt aacgccactt tgcaaggcat      60
ggaaaaatac ataactgaga atagaaaagt tcagatcaag gtcaggaaca agaaacagc     120 tgaataccaa acaggatatc tgtggtaagc ggttcctgcc ccggctcagg gccaagaaca    180
gatgagacag ctgagtgatg ggccaaacag gatatctgtg gtaagcagtt cctgccccgg    240
ctcggggcca agaacagatg gtccccagat gcggtccagc cctcagcagt ttctagtgaa    300
tcatcagatg tttccagggt gccccaagga cctgaaaatg accctgtacc ttatttgaac    360
taaccaatca gttcgcttct cgcttctgtt cgcgcgcttc cgctctccga gctcaataaa    420
agagcccaca cccctcact cggcgcgcca gtcttccgat agactgcgtc gcccgggtac     480
ccgtattccc aataaagcct cttgctgttt gcatccgaat cgtggtctcg ctgttccttg    540
ggagggtctc ctctgagtga ttgactaccc acgacggggg tctttcattt ggggggctcgt   600 ccgggatttg gagacccctg cccagggacc accgacccac caccgggagg taagctggcc    660
agcaacttat ctgtgtctgt ccgattgtct agtgtctatg tttgatgtta tgcgcctgcg    720
tctgtactag ttagctaact agctctgtat ctggcggacc cgtggtggaa ctgacgagtt    780
ctgaacaccc ggccgcaacc ctgggagacg tcccaggac tttgggggcc gttttgtgg      840 cccgacctga ggaagggagt cgatgtggaa tccgaccccg tcaggatatg tggttctggt    900
aggagacgag aacctaaaac agttcccgcc tccgtctgaa ttttgctttt cggtttggaa    960
ccgaagccgc gcgtcttgtc tgctgcagcg ctgcagcatc gttctgtgtt gtctctgtct   1020
gactgtgttt ctgtatttgt ctgaaaatta gggccagact gttaccactc ccttaagttt   1080
gaccttaggt cactggaaag atgtcgagcg gatcgctcac aaccagtcgg tagatgtcaa   1140
gaagagacgt tgggttacct tctgctctgc agaatggcca acctttaacg tcggatggcc   1200
gcgagacggc acctttaacc gagacctcat cacccaggtt aagatcaagg tcttttcacc   1260
tggcccgcat ggacacccag accaggtccc tacatcgtg acctgggaag ccttggcttt    1320
tgacccccct ccctgggtca agccctttgt acaccctaag cctccgcctc ctcttcctcc   1380

| | |
|---|---|
| atccgccccg tctctccccc ttgaacctcc tcgttcgacc ccgcctcgat cctcccttta | 1440 |
| tccagccctc actccttctc taggcgccgg aattcgcggc cgctacgtag tcgactcgct | 1500 |
| gtggaatgtg tgtcagttag ggtgtggaaa gtccccaggc tccccagcag gcagaagtat | 1560 |
| gcaaagcatg catctcaatt agtcagcaac caggtgtgga agtccccag gctccccagc | 1620 |
| aggcagaagt atgcaaagca tgcatctcaa ttagtcagca accatagtcc cgcccctaac | 1680 |
| tccgcccatc ccgcccctaa ctccgcccag ttccgcccat tctccgcccc atggctgact | 1740 |
| aattttttt atttatgcag aggccgaggc cgcctcggcc tctgagctat tccagaagta | 1800 |
| gtgaggaggc ttttttggag gcctaggctt ttgcaaaaag ctcgaagatc aattccgatc | 1860 |
| tgatcaagag acaggatgag gatcgtttcg catgattgaa caagatggat tgcacgcagg | 1920 |
| ttctccggcc gcttgggtgg agaggctatt cggctatgac tgggcacaac agacaatcgg | 1980 |
| ctgctctgat gccgccgtgt tccggctgtc agcgcagggg cgcccggttc ttttttgtcaa | 2040 |
| gaccgacctg tccggtgccc tgaatgaact gcaggacgag gcagcgcggc tatcgtggct | 2100 |
| ggccacgacg ggcgttcctt gcgcagctgt gctcgacgtt gtcactgaag cgggaaggga | 2160 |
| ctggctgcta ttgggcgaag tgccggggca ggatctcctg tcatctcacc ttgctcctgc | 2220 |
| cgagaaagta tccatcatgg ctgatgcaat gcggcggctg catacgcttg atccggctac | 2280 |
| ctgcccattc gaccaccaag cgaaacatcg catcgagcga gcacgtactc ggatggaagc | 2340 |
| cggtcttgtc gatcaggatg atctggacga agagcatcag gggctcgcgc cagccgaact | 2400 |
| gttcgccagg ctcaaggcgc gcatgcccga cggcgaggat ctcgtcgtga cccatggcga | 2460 |
| tgcctgcttg ccgaatatca tggtggaaaa tggccgcttt tctggattca tcgactgtgg | 2520 |
| ccggctgggt gtggcggacc gctatcagga catagcgttg gctacccgtg atattgctga | 2580 |
| agagcttggc ggcgaatggg ctgaccgctt cctcgtgctt tacggtatcg ccgctcccga | 2640 |
| ttcgcagcgc atcgccttct atcgccttct tgacgagttc ttctgagcgg gactctgggg | 2700 |
| ttcgtcgaga agcttgggcc catcgataaa ataaaagatt ttatttagtc tccagaaaaa | 2760 |
| ggggggaatg aaagacccca cctgtaggtt tggcaagcta gcttaagtaa cgccattttg | 2820 |
| caaggcatgg aaaaatacat aactgagaat agagaagttc agatcaaggt caggaacaga | 2880 |
| tggaacagct gaatatgggc caaacaggat atctgtggta agcagttcct gccccggctc | 2940 |
| agggccaaga acagatggaa cagctgaata tgggccaaac aggatatctg tggtaagcag | 3000 |
| ttcctgcccc ggctcagggc caagaacaga tggtccccag atgcggtcca gccctcagca | 3060 |
| gtttctagag aaccatcaga tgtttccagg gtgccccaag gacctgaaat gaccctgtgc | 3120 |
| cttatttgaa ctaaccaatc agttcgcttc tcgcttctgt tcgcgcgctt ctgctccccg | 3180 |
| agctcaataa aagagcccac aaccccctcac tcggggcgcc agtcctccga ttgactgagt | 3240 |
| cgcccgggta cccgtgtatc caataaaccc tcttgcagtt gcatccgact tgtggtctcg | 3300 |
| ctgttccttg gagggtctc ctctgagtga ttgactaccc gtcagcgggg gtctttcatt | 3360 |
| tgggggctcg tccgggatcg ggagacccct gcccagggac caccgaccca ccaccgggag | 3420 |
| gtaagctggc tgcctcgcgc gtttcggtga tgacggtgaa aacctctgac acatgcagct | 3480 |
| cccggagacg gtcacagctt gtctgtaagc ggatgccggg agcagacaag cccgtcaggg | 3540 |
| cgcgtcagcg ggtgttggcg ggtgtcgggg cgcagccatg acccagtcac gtagcgatag | 3600 |
| cggagtgtat actggcttaa ctatgcggca tcagagcaga ttgtactgag agtgcaccat | 3660 |
| atgcggtgtg aaataccgca cagatgcgta aggagaaaat accgcatcag gcgctcttcc | 3720 |
| gcttcctcgc tcactgactc gctgcgctcg gtcgttcggc tgcggcgagc ggtatcagct | 3780 |

```
cactcaaagg cggtaatacg gttatccaca gaatcagggg ataacgcagg aaagaacatg    3840
tgagcaaaag gccagcaaaa ggccaggaac cgtaaaaagg ccgcgttgct ggcgttttc     3900 cataggctcc gcccccctga cgagcatcac aaaaatcgac gctcaagtca gaggtggcga    3960
aacccgacag gactataaag ataccaggcg tttccccctg gaagctccct cgtgcgctct    4020
cctgttccga ccctgccgct taccggatac ctgtccgcct ttctcccttc gggaagcgtg    4080
gcgctttctc aatgctcacg ctgtaggtat ctcagttcgg tgtaggtcgt tcgctccaag    4140
ctgggctgtg tgcacgaacc ccccgttcag cccgaccgct gcgccttatc cggtaactat    4200
cgtcttgagt ccaacccggt aagacacgac ttatcgccac tggcagcagc cactggtaac    4260
aggattagca gagcgaggta tgtaggcggt gctacagagt tcttgaagtg gtggcctaac    4320
tacggctaca ctagaaggac agtatttggt atctgcgctc tgctgaagcc agttaccttc    4380
ggaaaaagag ttggtagctc ttgatccggc aaacaaacca ccgctggtag cggtggtttt    4440
tttgtttgca agcagcagat tacgcgcaga aaaaaaggat ctcaagaaga tcctttgatc    4500
ttttctacgg ggtctgacgc tcagtggaac gaaaactcac gttaagggat tttggtcatg    4560
agattatcaa aaaggatctt cacctagatc cttttaaatt aaaaatgaag ttttaaatca    4620
atctaaagta tatatgagta aacttggtct gacagttacc aatgcttaat cagtgaggca    4680
cctatctcag cgatctgtct atttcgttca tccatagttg cctgactccc cgtcgtgtag    4740
ataactacga tacgggaggg cttaccatct ggccccagtg ctgcaatgat accgcgagac    4800
ccacgctcac cggctccaga tttatcagca ataaaccagc cagccggaag ggccgagcgc    4860
agaagtggtc ctgcaacttt atccgcctcc atccagtcta ttaattgttg ccgggaagct    4920
agagtaagta gttcgccagt taatagtttg cgcaacgttg ttgccattgc tgcaggcatc    4980
gtggtgtcac gctcgtcgtt tggtatggct tcattcagct ccggttccca acgatcaagg    5040
cgagttacat gatcccccat gttgtgcaaa aaagcggtta gctccttcgg tcctccgatc    5100
gttgtcagaa gtaagttggc cgcagtgtta tcactcatgg ttatggcagc actgcataat    5160
tctcttactg tcatgccatc cgtaagatgc ttttctgtga ctggtgagta ctcaaccaag    5220
tcattctgag aatagtgtat gcggcgaccg agttgctctt gcccggcgtc aacacgggat    5280
aataccgcgc cacatagcag aactttaaaa gtgctcatca ttggaaaacg ttcttcgggg    5340
cgaaaactct caaggatctt accgctgttg agatccagtt cgatgtaacc cactcgtgca    5400
cccaactgat cttcagcatc ttttactttc accagcgttt ctgggtgagc aaaaacagga    5460
aggcaaaatg ccgcaaaaaa gggaataagg gcgacacgga aatgttgaat actcatactc    5520
ttcctttttc aatattattg aagcatttat cagggttatt gtctcatgag cggatacata    5580
tttgaatgta tttagaaaaa taaacaaata ggggttccgc gcacatttcc ccgaaaagtg    5640
ccacctgacg tctaagaaac cattattatc atgacattaa cctataaaaa taggcgtatc    5700
acgaggccct ttcgtcttca agaattcata ccagatcacc gaaaactgtc tccaaatgt     5760 gtccccctca cactcccaaa ttcgcgggct tctgcctctt agaccactct accctattcc    5820
ccacactcac cggagccaaa gccgcggccc ttccgtttct ttgct                    5865
```

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 8

```
gttaacgtgg tcaagcttgt gacggtgacc cgccgccacc                          40

<210> SEQ ID NO 9
<211> LENGTH: 78
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 9
atggtctcag ccacccgctc gcttctctgt gcagcgctgc ctgtgctggc cacctctaga    60
caagccacag gggggccc                                                  78

<210> SEQ ID NO 10
<211> LENGTH: 123
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 10
gctagcctgc cccagaagtc gcagcacggc cggacccaag atgaaaaccc agtagtccat    60
ttcttcaaga acattgtgac acctcgaaca ccacctccat cccaagggaa ggggagaggc   120
ctt                                                                 123

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 11
gtccatttct tcaagaacat tgtgacacct cgaacacca                           39

<210> SEQ ID NO 12
<211> LENGTH: 3
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 12 aag                                                                  3

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 13
tgaataacca taatgatggg ctataccgcg gccgcc                              36

<210> SEQ ID NO 14
<211> LENGTH: 78
<212> TYPE: DNA
<213> ORGANISM: Artificial Sequence
<220> FEATURE:
```

<223> OTHER INFORMATION: Description of Artificial Sequence: Synthetic
      construct

<400> SEQUENCE: 14
atggtctcag ccacccgctc gcttctctgt gcagcgctgc ctgtgctggc cacctctaga    60
caagccacag gggggccc                                                  78

<210> SEQ ID NO 15
<211> LENGTH: 41
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 15

Ala Ser Leu Pro Gln Lys Ser Gln His Gly Arg Thr Gln Asp Glu Asn
 1               5                  10                  15

Pro Val Val His Phe Phe Lys Asn Ile Val Thr Pro Arg Thr Pro Pro
            20                  25                  30

Pro Ser Gln Gly Lys Gly Arg Gly Leu
        35                  40

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 16
taggatcctt gaataggtaa ggttgctacc ccgcggtg                            38

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 17

Val His Phe Phe Lys Asn Ile Val Thr Pro Arg Thr Pro
 1               5                  10

<210> SEQ ID NO 18
<211> LENGTH: 107
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cggcgactac aagaccacca tctgcggcaa gggcctgagc gcaacggtaa cagggggcca    60
gaaggggagg ggttccagag gccaacatca agctcattct ctcgagc                 107

<210> SEQ ID NO 19
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 19
gagcttgatg ttggcctctg gaacccctcc ccttctggcc ccctgttacc gttgcgctca      60
ggcccttgcc gcagatggtg gtcttgtagt cgccgggcc                             99

<210> SEQ ID NO 20
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gggtgtgtca ttgtttggga aaatggctag gacatcccga caagtttgtg ggcatcacct      60
atgctagcct taagtaggat ccttgaatag gta                                   93

<210> SEQ ID NO 21
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agcttaccta ttcaaggatc ctacttaagg ctagcatagg tgatgccca                  49

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
caaacttgtc gggatgtcct agccattttc ccaaacaatg acacacccgc tcgagagaat      60

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gatttaggtg acactatag                                                   19

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
taatacgact cactataggg                                                  20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                              primer

<400> SEQUENCE: 25
gcgactacaa gaccaccatc t                                               21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
taaggctagc ataggtgatg                                                 20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcgactacaa gaccaccatc t                                               21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
taaggctagc ataggtgatg                                                 20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gctagcctgc cccagaagtc g                                               21

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cttaaggcct ctccccttcc cttg                                            24

<210> SEQ ID NO 31
<211> LENGTH: 317
<212> TYPE: DNA
<213> ORGANISM: Artificial Sequence
<220> FEATURE:
<223> OTHER INFORMATION: Description of Artificial Sequence: Synthetic
      construct
<220> FEATURE:
```

```
<221> NAME/KEY: CDS
<222> LOCATION: (28)..(285)

<400> SEQUENCE: 31
gatggtgacc ggagatctgc cgccacc atg ggg gcg atg gct ccg cgc acg ctg      54
                               Met Gly Ala Met Ala Pro Arg Thr Leu
                                 1               5 ctc ctg ctg ctg gcg gcc gcc ctg gcc ccg act cag acc cgc gcg ggg       102
Leu Leu Leu Leu Ala Ala Ala Leu Ala Pro Thr Gln Thr Arg Ala Gly
 10              15                  20                  25 ccc ggc gac tac aag acc acc atc tgc ggc aag ggc ctg agc gca acg       150
Pro Gly Asp Tyr Lys Thr Thr Ile Cys Gly Lys Gly Leu Ser Ala Thr
             30                  35                  40 gta aca ggg ggc cag aag ggg agg ggt tcc aga ggc caa cat caa gct       198
Val Thr Gly Gly Gln Lys Gly Arg Gly Ser Arg Gly Gln His Gln Ala
             45                  50                  55 cat tct ctc cag cgg gtg tgt cat tgt ttg gga aaa tgg cta gga cat       246
His Ser Leu Gln Arg Val Cys His Cys Leu Gly Lys Trp Leu Gly His
         60                  65                  70 ccc gac aag ttt gtg ggc atc acc tat gct agc ctt aag taggatcctt        295
Pro Asp Lys Phe Val Gly Ile Thr Tyr Ala Ser Leu Lys
     75                  80                  85 gaataggtaa gcttgctagc cc                                              317

<210> SEQ ID NO 32
<211> LENGTH: 86
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 32

Met Gly Ala Met Ala Pro Arg Thr Leu Leu Leu Leu Ala Ala Ala
  1               5                  10                  15

Leu Ala Pro Thr Gln Thr Arg Ala Gly Pro Gly Asp Tyr Lys Thr Thr
                 20                  25                  30

Ile Cys Gly Lys Gly Leu Ser Ala Thr Val Thr Gly Gly Gln Lys Gly
             35                  40                  45

Arg Gly Ser Arg Gly Gln His Gln Ala His Ser Leu Gln Arg Val Cys
         50                  55                  60

His Cys Leu Gly Lys Trp Leu Gly His Pro Asp Lys Phe Val Gly Ile
 65                  70                  75                  80

Thr Tyr Ala Ser Leu Lys
                 85

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agctgatcga tggtgac                                                     17

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 34
aagcttgcta gcccgcggtg gcc                                              23

<210> SEQ ID NO 35
<211> LENGTH: 280
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (41)..(244)

<400> SEQUENCE: 35
gttaacgtgg tcaagcttgt gacggtgacc cgccgccacc atg gtc tca gcc acc        55
                                            Met Val Ser Ala Thr
                                            1               5 cgc tcg ctt ctc tgt gca gcg ctg cct gtg ctg gcc acc tct aga caa       103
Arg Ser Leu Leu Cys Ala Ala Leu Pro Val Leu Ala Thr Ser Arg Gln
            10                  15                  20 gcc aca ggg ggg ccc gct agc ctg ccc cag aag tcg cag cac ggc cgg       151
Ala Thr Gly Gly Pro Ala Ser Leu Pro Gln Lys Ser Gln His Gly Arg
        25                  30                  35 acc caa gat gaa aac cca gta gtc cat ttc ttc aag aac att gtg aca       199
Thr Gln Asp Glu Asn Pro Val Val His Phe Phe Lys Asn Ile Val Thr
    40                  45                  50 cct cga aca cca cct cca tcc caa ggg aag ggg aga ggc ctt aag           244
Pro Arg Thr Pro Pro Pro Ser Gln Gly Lys Gly Arg Gly Leu Lys
55                  60                  65 tgaataacca taatgatggg ctataccgcg gccgcc                                280

<210> SEQ ID NO 36
<211> LENGTH: 68
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 36

Met Val Ser Ala Thr Arg Ser Leu Leu Cys Ala Ala Leu Pro Val Leu
1               5                   10                  15

Ala Thr Ser Arg Gln Ala Thr Gly Gly Pro Ala Ser Leu Pro Gln Lys
            20                  25                  30

Ser Gln His Gly Arg Thr Gln Asp Glu Asn Pro Val Val His Phe Phe
        35                  40                  45

Lys Asn Ile Val Thr Pro Arg Thr Pro Pro Pro Ser Gln Gly Lys Gly
    50                  55                  60

Arg Gly Leu Lys
65

<210> SEQ ID NO 37
<211> LENGTH: 313
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (18)..(275)

-continued

```
<400> SEQUENCE: 37
ggtgacccgc cgccacc atg gtc tca gcc acc cgc tcg ctt ctc tgt gca         50
                   Met Val Ser Ala Thr Arg Ser Leu Leu Cys Ala
                    1               5                  10 gcg ctg cct gtg ctg gcc acc tct aga caa gcc aca ggg ggg ccc ggc        98
Ala Leu Pro Val Leu Ala Thr Ser Arg Gln Ala Thr Gly Gly Pro Gly
             15                  20                  25 gac tac aag acc acc atc tgc ggc aag ggc ctg agc gca acg gta aca       146
Asp Tyr Lys Thr Thr Ile Cys Gly Lys Gly Leu Ser Ala Thr Val Thr
         30                  35                  40 ggg ggc cag aag ggg agg ggt tcc aga ggc caa cat caa gct cat tct       194
Gly Gly Gln Lys Gly Arg Gly Ser Arg Gly Gln His Gln Ala His Ser
     45                  50                  55 ctc gag cgg gtg tgt cat tgt ttg gga aaa tgg cta gga cat ccc gac       242
Leu Glu Arg Val Cys His Cys Leu Gly Lys Trp Leu Gly His Pro Asp
 60                  65                  70                  75 aag ttt gtg ggc atc acc tat gct agc ctt aag taggatcctt gaataggtaa     295
Lys Phe Val Gly Ile Thr Tyr Ala Ser Leu Lys
                 80                  85 ggttgctacc ccgcggtg                                                    313

<210> SEQ ID NO 38
<211> LENGTH: 86
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 38

Met Val Ser Ala Thr Arg Ser Leu Leu Cys Ala Ala Leu Pro Val Leu
 1               5                  10                  15

Ala Thr Ser Arg Gln Ala Thr Gly Gly Pro Gly Asp Tyr Lys Thr Thr
             20                  25                  30

Ile Cys Gly Lys Gly Leu Ser Ala Thr Val Thr Gly Gly Gln Lys Gly
         35                  40                  45

Arg Gly Ser Arg Gly Gln His Gln Ala His Ser Leu Glu Arg Val Cys
     50                  55                  60

His Cys Leu Gly Lys Trp Leu Gly His Pro Asp Lys Phe Val Gly Ile
 65                  70                  75                  80

Thr Tyr Ala Ser Leu Lys
                 85
```